US011634747B2

(12) United States Patent
Fernando et al.

(10) Patent No.: US 11,634,747 B2
(45) Date of Patent: Apr. 25, 2023

(54) PRESERVATION OF FETAL NUCLEIC ACIDS IN MATERNAL PLASMA

(75) Inventors: M. Rohan Fernando, Omaha, NE (US); Kate Chao-Wei Chen, Indianapolis, IN (US)

(73) Assignee: STRECK LLC, La Vista, NE (US)

( * ) Notice: Subject to any disclaimer, the term of this patent is extended or adjusted under 35 U.S.C. 154(b) by 136 days.

(21) Appl. No.: 12/689,370

(22) Filed: Jan. 19, 2010

(65) Prior Publication Data

US 2010/0184069 A1 Jul. 22, 2010

Related U.S. Application Data

(60) Provisional application No. 61/227,529, filed on Jul. 22, 2009, provisional application No. 61/146,065, filed on Jan. 21, 2009.

(51) Int. Cl.
*C12Q 1/6806* (2018.01)

(52) U.S. Cl.
CPC .................. *C12Q 1/6806* (2013.01)

(58) Field of Classification Search
CPC combination set(s) only.
See application file for complete search history.

(56) References Cited

U.S. PATENT DOCUMENTS

| | | | |
|---|---|---|---|
| 1,432,249 A | 10/1922 | Robert | |
| 1,922,799 A | 8/1933 | Gaus | |
| 2,250,666 A | 7/1941 | Webb | |
| 2,690,624 A | 10/1954 | Phillips | |
| 2,930,570 A | 3/1960 | Leedy | |
| 3,781,120 A | 12/1973 | Engelhardt | |
| 3,867,521 A | 2/1975 | Miskel et al. | |
| 3,872,730 A | 3/1975 | Ringrose et al. | |
| 3,874,384 A | 4/1975 | Deindoerfer | |
| 3,879,295 A | 4/1975 | Glover et al. | |
| 3,973,913 A | 8/1976 | Louderback | |
| 3,994,085 A | 11/1976 | Groselak et al. | |
| 4,043,453 A | 8/1977 | Greenlee | |
| 4,318,090 A | 3/1982 | Narlow et al. | |
| 4,513,522 A | 4/1985 | Selenke | |
| 4,515,890 A | 5/1985 | Manderino et al. | |
| 4,579,759 A | 4/1986 | Breuers | |
| 4,584,219 A | 4/1986 | Baartmans | |
| 4,675,159 A | 6/1987 | Al-Sioufi | |
| 4,884,827 A | 12/1989 | Kelley | |
| 4,921,277 A | 5/1990 | McDonough | |
| 5,000,484 A | 3/1991 | Phelan et al. | |
| 5,060,672 A | 10/1991 | Sandor et al. | |
| 5,110,908 A | 5/1992 | Ch et al. | |
| 5,135,125 A | 8/1992 | Andel et al. | |
| 5,196,182 A | 3/1993 | Ryan | |
| 5,213,765 A | 5/1993 | Kasai et al. | |
| 5,250,438 A | 10/1993 | Ryan | |
| 5,257,633 A | 11/1993 | Vogler et al. | |
| 5,260,048 A | 11/1993 | Ryan | |
| 5,343,647 A | 9/1994 | Bulka | |
| 5,366,249 A | 11/1994 | Diemert | |
| 5,447,842 A | 9/1995 | Simons | |
| 5,457,024 A | 10/1995 | Goldbard | |
| 5,459,073 A | 10/1995 | Ryan | |
| 5,459,253 A | 10/1995 | Wolin et al. | |
| 5,460,797 A | 10/1995 | Ryan | |
| 5,468,022 A | 11/1995 | Linder et al. | |
| 5,490,658 A | 2/1996 | Coward et al. | |
| 5,501,954 A | 3/1996 | Mahr | |
| 5,512,343 A | 4/1996 | Shaw | |
| 5,540,358 A | 7/1996 | Wiles et al. | |
| 5,560,657 A | 10/1996 | Morgan | |
| 5,614,391 A | 3/1997 | Franskovich et al. | |
| 5,618,664 A | 4/1997 | Kiessling | |
| 5,629,147 A | 5/1997 | Asgari | |
| D382,343 S | 8/1997 | Wandell et al. | |
| 5,654,054 A * | 8/1997 | Tropsha ............... | B01L 3/5082 206/524.2 |
| 5,688,516 A | 11/1997 | Raad | |
| 5,731,156 A | 3/1998 | Golbus | |
| 5,783,093 A | 7/1998 | Holme | |
| 5,811,099 A | 9/1998 | Ryan | |
| 5,817,519 A | 10/1998 | Zelmanovic et al. | |
| 5,849,517 A * | 12/1998 | Ryan ......................... | 435/40.51 |

(Continued)

FOREIGN PATENT DOCUMENTS

| | | |
|---|---|---|
| CA | 2406463 | 1/2001 |
| DE | 19928820 | 6/1999 |

(Continued)

OTHER PUBLICATIONS

Chung et al (Clinical Chemistry (2005) vol. 51 pp. 655-658).*
QIAamp DNA blood midi kit and QIAamp DNA blood Maxi kit handbook (2001).*
Chan et al (Clinical Chemistry (2004) vol. 50, pp. 88-92).*
MSDS for imidazolidinyl urea (sigma Aldrich (May 7, 2015).*
MSDS for glycine (sigma Aldrich (May 7, 2015).*
The MSDS for Ethylenediaminetetraacetic acid (sigma Aldrich (May 7, 2015).*
Burkhard Kirste (http://www.chemie.fu-berlin.de/chemistry/bio/aminoacid/glycin_en.html, Jan. 23, 1998 ).*
Wright (Human Reproduction Updates (2009) vol. 15, pp. 139-151).*
Dean (proceedings national Academy of Sciences (2002) vol. 99, pp. 5261-5266).*
Li (JAMA (2005) vol. 293, pp. 843-849).*
Swarup (FEBS Letters (2007) vol. 581, pp. 795-799).*
Lo (Am J Humn Genet (1998) vol. 62, pp. 768-775).*

(Continued)

*Primary Examiner* — Steven Pohnert
(74) *Attorney, Agent, or Firm* — Marshall, Gerstein & Borun LLP

(57) ABSTRACT

A method for preserving and processing fetal nucleic acids located within maternal plasma is disclosed, wherein a sample of maternal blood containing fetal nucleic acids is treated to reduce both cell lysis of the maternal blood cells and deoxyribonuclease (DNase) and ribonuclease (RNase) activity within the fetal nucleic acids. The treatment of the sample aids in increasing the amount of fetal nucleic acids that can be identified and tested while maintaining the structure and integrity of the fetal nucleic acids.

20 Claims, 5 Drawing Sheets

(56) References Cited

U.S. PATENT DOCUMENTS

| | | |
|---|---|---|
| 5,858,699 A | 1/1999 | Granger |
| 5,861,253 A | 1/1999 | Asgari et al. |
| 5,906,744 A | 5/1999 | Carroll et al. |
| 5,962,234 A | 10/1999 | Golbus |
| 5,976,014 A | 11/1999 | Petrick et al. |
| 5,977,153 A | 11/1999 | Camiener |
| 5,985,572 A | 11/1999 | Macfarlane |
| 6,013,240 A | 1/2000 | Behr et al. |
| 6,030,767 A | 2/2000 | Wagner |
| 6,043,032 A | 3/2000 | Yamagishi et al. |
| 6,072,086 A | 6/2000 | James et al. |
| 6,074,827 A | 6/2000 | Nelson |
| 6,077,235 A | 6/2000 | Serpentino et al. |
| 6,125,563 A | 10/2000 | Girerd |
| 6,128,840 A | 10/2000 | Boisvert |
| 6,168,922 B1 | 1/2001 | Harvey et al. |
| 6,177,163 B1 | 1/2001 | Block et al. |
| 6,190,609 B1 | 2/2001 | Chapman |
| 6,197,539 B1 | 3/2001 | Granger |
| 6,197,540 B1 | 3/2001 | Granger |
| 6,210,889 B1 | 4/2001 | Drouin et al. |
| 6,218,531 B1 | 4/2001 | Ekenberg |
| 6,251,638 B1 | 6/2001 | Umansky et al. |
| 6,258,540 B1 | 7/2001 | Lo et al. |
| 6,287,820 B1 | 9/2001 | Umansky et al. |
| 6,337,189 B1 | 1/2002 | Ryan |
| 6,365,362 B1 | 4/2002 | Terstappen et al. |
| 6,527,242 B1 | 3/2003 | Kennedy |
| 6,527,957 B1 | 3/2003 | Deniega |
| 6,551,267 B1 | 4/2003 | Cohen et al. |
| 6,560,847 B2 | 5/2003 | Ohlsson |
| 6,579,672 B1 | 6/2003 | Granger |
| 6,581,973 B2 | 6/2003 | Levine et al. |
| 6,602,718 B1 | 8/2003 | Augello et al. |
| 6,617,170 B2 | 9/2003 | Augello et al. |
| 6,617,180 B1 | 9/2003 | Wang |
| 6,623,983 B1 | 9/2003 | Terstappen et al. |
| 6,630,301 B1 | 10/2003 | Gocke et al. |
| 6,645,731 B2 | 11/2003 | Terstappen et al. |
| 6,664,056 B2 | 12/2003 | Lo et al. |
| 6,759,217 B2 | 7/2004 | Kopreski et al. |
| 6,821,789 B2 | 11/2004 | Augello et al. |
| 6,860,513 B2 | 3/2005 | Kaufman |
| 6,884,573 B2 | 4/2005 | Fischer |
| 6,916,634 B2 | 7/2005 | Kopreski |
| 6,939,671 B2 | 9/2005 | Kopreski |
| 6,994,790 B2 | 2/2006 | Corbin |
| 7,022,478 B2 | 4/2006 | Rainer et al. |
| 7,044,941 B2 | 5/2006 | Mathias |
| 7,208,275 B2 | 4/2007 | Gocke et al. |
| 7,267,980 B1 | 9/2007 | Mortari |
| 7,282,371 B2 | 10/2007 | Helftenbein |
| 7,288,380 B1 | 10/2007 | Gocke et al. |
| 7,318,293 B2 | 1/2008 | Ardern |
| 7,332,277 B2 | 2/2008 | Dhallan |
| 7,332,288 B2 | 2/2008 | Terstappen et al. |
| 7,358,039 B2 | 4/2008 | Fischer et al. |
| 7,390,663 B2 | 6/2008 | Ryan et al. |
| 7,398,999 B2 | 7/2008 | Kaufman |
| 7,419,832 B2 | 9/2008 | Hunsley et al. |
| 7,442,506 B2 | 10/2008 | Dhallan |
| 7,445,901 B2 | 11/2008 | Kudlicki et al. |
| 7,478,513 B2 | 1/2009 | Baldwin |
| 7,569,350 B2 | 8/2009 | Gocke et al. |
| 7,651,838 B2 | 1/2010 | Paterlini-Brechot |
| 7,767,460 B2 | 8/2010 | Hunsley et al. |
| 8,586,306 B2 | 11/2013 | Fernando |
| 9,040,255 B2 | 5/2015 | Tsinberg |
| 9,120,849 B2 | 9/2015 | Chiklis et al. |
| 9,127,048 B2 | 9/2015 | Chiklis et al. |
| 9,926,950 B2 | 3/2018 | Fernando |
| 10,091,984 B2 | 10/2018 | Fernando |
| 2001/0018192 A1 | 8/2001 | Terstappen et al. |
| 2001/0049895 A1 | 12/2001 | Burke |
| 2001/0051341 A1 | 12/2001 | Lo et al. |
| 2002/0045196 A1 | 4/2002 | Mahoney et al. |
| 2002/0066216 A1 | 6/2002 | DeLaCruz |
| 2002/0086346 A1 | 7/2002 | Ryan |
| 2002/0119503 A1 | 8/2002 | Ryan et al. |
| 2003/0232377 A1 | 12/2003 | Thomas |
| 2004/0014107 A1* | 1/2004 | Garcia-Blanco ....... C07K 16/10 435/6.14 |
| 2004/0038424 A1 | 2/2004 | Maples |
| 2004/0137417 A1* | 7/2004 | Ryan ................ 435/2 |
| 2005/0029559 A9 | 2/2005 | Ahn et al. |
| 2005/0049793 A1 | 3/2005 | Paterlini-Brechot |
| 2005/0232377 A1 | 3/2005 | Paterlini-Brechot |
| 2005/0164208 A1* | 7/2005 | Poulin ................ 435/6 |
| 2005/0181353 A1 | 8/2005 | Rao et al. |
| 2005/0181463 A1 | 8/2005 | Rao et al. |
| 2005/0277204 A1 | 12/2005 | Hollis et al. |
| 2006/0008807 A1 | 1/2006 | O'Hara |
| 2006/0105372 A1 | 5/2006 | Bair et al. |
| 2006/0194192 A1 | 8/2006 | Rao |
| 2006/0210429 A1 | 9/2006 | Hunsley et al. |
| 2007/0111233 A1 | 5/2007 | Bianchi et al. |
| 2007/0134658 A1 | 6/2007 | Bohmer |
| 2007/0178478 A1 | 8/2007 | Dhallan |
| 2007/0202525 A1 | 8/2007 | Quake et al. |
| 2007/0243549 A1* | 10/2007 | Bischoff ................ C07K 16/18 435/6.19 |
| 2007/0251337 A1 | 11/2007 | Reed et al. |
| 2007/0298406 A1 | 12/2007 | Martorell et al. |
| 2008/0020390 A1 | 1/2008 | Mitchell et al. |
| 2008/0057502 A1 | 3/2008 | Kopreski |
| 2008/0081689 A1 | 4/2008 | Seelig et al. |
| 2008/0096217 A1 | 4/2008 | Kopreski |
| 2008/0102470 A1 | 5/2008 | Dawson et al. |
| 2008/0108071 A1 | 5/2008 | Thompson |
| 2008/0119645 A1 | 5/2008 | Griffey et al. |
| 2008/0206866 A1 | 8/2008 | Zieglschmid et al. |
| 2008/0261292 A1 | 10/2008 | Kopreski |
| 2008/0318801 A1 | 12/2008 | Leung et al. |
| 2009/0034446 A1 | 2/2009 | Adams et al. |
| 2009/0081678 A1 | 3/2009 | Ryan et al. |
| 2009/0215036 A1 | 8/2009 | Stropp et al. |
| 2009/0308303 A1 | 12/2009 | Burlando |
| 2010/0167271 A1 | 7/2010 | Ryan |
| 2010/0184069 A1 | 7/2010 | Fernando et al. |
| 2010/0209930 A1 | 8/2010 | Fernando |
| 2010/0216153 A1 | 8/2010 | Lapidus |
| 2010/0317107 A1 | 12/2010 | Ryan |
| 2011/0027771 A1 | 2/2011 | Deng |
| 2011/0053208 A1 | 3/2011 | Reiss |
| 2011/0111410 A1 | 5/2011 | Ryan et al. |
| 2012/0164676 A1 | 6/2012 | Tsinberg |
| 2012/0308990 A1 | 12/2012 | TerMaat |
| 2013/0034860 A1 | 2/2013 | Fernando |
| 2014/0054508 A1 | 2/2014 | Fernando |
| 2014/0080112 A1 | 3/2014 | Ryan et al. |
| 2014/0199681 A1 | 7/2014 | Ryan et al. |
| 2015/0301037 A1 | 10/2015 | Tsinberg et al. |
| 2016/0143268 A1 | 5/2016 | Ryan |
| 2016/0174544 A1 | 6/2016 | Fernando et al. |

FOREIGN PATENT DOCUMENTS

| | | |
|---|---|---|
| EP | 1 031 626 A1 | 8/2000 |
| EP | 1207208 A2 | 5/2002 |
| EP | 1 217 372 A1 | 6/2002 |
| EP | 1816461 A1 | 8/2007 |
| EP | 1 889 921 A2 | 2/2008 |
| EP | 1425294 B1 | 7/2008 |
| EP | 2228453 A1 | 9/2010 |
| EP | 2216416 | 11/2010 |
| EP | 2411808 B1 | 2/2012 |
| EP | 2674502 A1 | 12/2013 |
| WO | 93/05650 | 4/1993 |
| WO | 94/02646 | 2/1994 |
| WO | 95/26417 | 10/1995 |
| WO | 98/02528 A1 | 1/1998 |
| WO | 98/02740 A1 | 1/1998 |
| WO | 98/59042 A1 | 12/1998 |
| WO | 00/06780 A1 | 2/2000 |

(56) References Cited

FOREIGN PATENT DOCUMENTS

| WO | 00/75647 | 12/2000 |
|---|---|---|
| WO | 00/77235 | 12/2000 |
| WO | 01/79851 | 10/2001 |
| WO | 01/98542 | 12/2001 |
| WO | 02/055985 | 7/2002 |
| WO | 03/018757 A2 | 3/2003 |
| WO | 03/019141 A2 | 6/2003 |
| WO | 03/069344 | 8/2003 |
| WO | 03/095974 | 11/2003 |
| WO | 2006/100063 A2 | 9/2006 |
| WO | 2007/022483 A2 | 2/2007 |
| WO | 2008/107724 A2 | 9/2008 |
| WO | 2008/111981 A1 | 9/2008 |
| WO | 2010/096323 A1 | 8/2010 |
| WO | 2010/123908 A1 | 10/2010 |
| WO | 2011/014741 | 2/2011 |
| WO | 2011/057184 | 5/2011 |
| WO | 2011/082415 | 7/2011 |
| WO | 2011/082415 A2 | 7/2011 |
| WO | 2012/145662 A1 | 10/2012 |
| WO | 2012/166913 A1 | 12/2012 |
| WO | 2013/086428 A1 | 6/2013 |
| WO | 2013/123030 A3 | 8/2013 |
| WO | 2014/029791 A1 | 2/2014 |

OTHER PUBLICATIONS

Merriam-Webster.com (https://www.merriam-webster.com/dictionary/constant (downloaded May 28, 2020)).*
Lee (Transfusion vol. 41, Feb. 2001, pp. 276-282).*
Holodniy (Journal ofclinicalmicrobiology, Jun. 1995, p. 1562-1566).*
Voronina (Applied Biochemistry and Microbiology, 2008, vol. 44, No. 2, pp. 218-222. ).*
Fernando (Prenat Diagn 2010; 30: 418-424).*
Trezl (Molecular and Cellular Biochemistry (2003) vol. 244, pp. 167-176).*
Clinic Chimica Acta 397 (2008) 60-64—"Effect of Formaldehyde Treatment on recovery of cell-free fetal DNA from Maternal Plasma at different Processing Times".
Clinical Chemistry 51, No. 3, 2005, "Lack of Dramatic Enrichment of Fetal DNA in Maternal Plasma by Formaldehyde Treatment".
Annals of the New York Academy of Sciences: vol. 945, Issue Circulating Nucleic Acids in Plasma or Serum II, pp. 1-291 (Sep. 2001).
Clinical Chemistry 45:10, 1747-1751 (1999), "Increased Fetal DNA Concentrations in the Plasma of Pregnant Women Carrying Fetuses with Trisomy 21".
Clinical Chemistry 46, No. 8, 2000, "Molecular Testing of Urine: Catching DNA on the way out".
Clinical Chemistry 46;8, 1078-1084 (2000) "Genetic Analysis of DNA Excreted in Urine: a New Approach for Detecting Specific Genomic DNA Sequences from Cells Dying in an Organism".
Fetal Nucleic Acids in Maternal Plasma, Toward the Development of Noninvasive Prenatal Diagnosis of Fetal Chromosomal Aneuploidies, Y.M. Dennis Lo, 2008 New York Academy of Sciences.
"Methods to Increase the Prercentage of Free Fetal DNA Recovered from the Maternal Circulation", JAMA, Mar. 3, 2004—vol. 291, No. 9.
Clinical Chemistry 47:9, 1607-1613 (2001) "Effects of Blood-Processing Protocols on Fetal and Total DNA Quantification in Maternal Plasma".
Treatment of Maternal Blood Samples with Formaldehyde does not alter the proportion; Clinical Chemistry/ 209163625; Jan. 19, 2012.
Prenatal Diagnosis Prenat Diagn 2000; 20: 886-889; "Apoptosis in Fetal Nucleated Erythrocytes Circulating in Maternal Blood".
"Down syndrome and Cell-Free Fetal DNA in Archived Maternal Serum" Thomas Lee, MD (AM J. Obstet Gynecol 2002; 187: 1217-21).
Am J. Hum. Genet. 61 :822-829, 1997; "PCR Quantification of Fetal Cells in Maternal Blood in Normal and Aneuploid Pregnancies".
"Fetal Cell-Free Plasma DNA Concentrations in Maternal Blood are Stable 24 hours after" Clinical-Chemistry (Jan. 19, 2012).
Technical Briefs Treatment of Maternal Blood Samples with Formaldehyde does not Alter the Proportion of Circulatory Fetal Nucleic Acids (DNA and mRNA) in Maternal Plasma) Nov. 2005.
Search Report and Written Opinion of co-pending PCT Application NO. US2010/55815, filed on Nov. 8, 2010.
European Search Report dated Jul. 29, 2010 in corresponding Application No. 10000518.0-2402.
European Office Action dated Mar. 5, 2011 in corresponding application No. 10000518.0-2402.
Co-pending U.S. Appl. No. 12/646,204, filed Dec. 23, 2009, Published as US 2010/0167271 A1 on Jul. 1, 2010.
Co-pending U.S. Appl. No. 12/704,030, filed Feb. 11, 2010, Published as US 2010/0209930 on Aug. 19, 2010.
Co-pending U.S. Appl. No. 12/941,437, filed Nov. 8, 2010, Published as 2011/0111410A1 on May 12, 2011.
Machaca et al. Characterization of apoptosis-like endonuclease activity in avian thymocytes, Biology of the Cell, Jan. 1, 1992, 15-22, 76(1), Elsevier, Paris France.
Holford et al, Stability of beta-actin mRNA in plasma, Annals of the New York Academy of Science, Aug. 2008, 108-111, 1137.
Pinzani et al., Circulating nucleic acids in cancer and pregnancy, Methods: a Companion to Methods in Enzymology, Apr. 1, 2010, 302-307, 40 (4), Academic Press Inc., New York.
Puren et al., Laboratory operations, specimen processing, and handling for viral load testing and surveillance, Journal of Infectious Diseases, Apr. 15, 2010, S27-S36, 201 (supp 1), University of Chicago Press, Chicago Il.
Palmer, et al., Flow cytometric determination of residual white blood cell, levels in preserved samples from leukoreduced blood products, Transfusion, Jan. 2008, 118-128, 48(1).
Chan et al, Hypermethylated RASSFIA in maternal Plasma: a Universal Fetal DNA Marker that Improves the Reliability of Noninvasive Prenatal Diagnosis, Clinical Chemistry, 2006, 2211-2218, 52(12).
Lee et al. Survival of Donor Leukocyte Subpopulations in Immunocompetent Transfusion Recipients: Frequent Long-Term Microchimerism in Severe Trauma Patients, Blood, 1999, 3127-3139, 93.
Madabusi et al., RNA extraction for arrays, Methods in Enzymology, 2006,1-14, 411.
US Food and Drug Adminstration, Draft Guidance for Industry: Pre-Storage Leukocyte Reduction of Whole Blood and Blood Components Intended for Transfusion, Vaccines. Blood & Biologics, available at: www.fda.gov/biologicsbloodvaccines/guidance compliance regulatoryinformation/guidances/blood/ucm076769.htm, last accessed Apr. 13, 2011.
Search Report and Written Opinion of corresponding PCT Application No. US2010/023859, filed on Feb. 11, 2010.
Bina-Stein, et al., Aurintricarboxylic Acid Is a Nonspecific Enzyme Inhibitor, Department of Chemistry, Yale University, New Haven, Connecticut. 1975, 12:191-193.
Ding, et al., MS Analysis of Single-Nucleotide Differences in Circulating Nucleic Acids: Applicatin to Noninvasive Prenatal Diagnosis, 2004, 101:10762-10767.
Bianchi, Invited Editorial Fetal DNA in Maternal Plasma: The Plot Thickens and the Placental Barrier Thins, by The American Society of Human Genetics, 62:763-764, 1998.
Li, et al., Detection of Paternally Inherited Fetal Point Mutations for β-Thalassemia Using Size-Fractionated Cell-Free DNA in Maternal Plasma, available at: www.jama.com, 2005, 293:843-849.
Lo, Fetal DNA in Maternal Plasma: Biology and Diagnostic Applications, Clinical Chemistry 46:12 1903-1906, 2000.
Lo, et al., Quantitative Analysis of Fetal DNA in Maternal Plasma and Serum: Implications for Noninvasive Prenatal Diagnosis, by The American Society of Human Genetics, 62:768-775, 1998.
Peril, et al., Fetal DNA in Maternal Plasma: Emerging Clinical Applications, by The American College of Obstetricians and Gynecologists, 98:483-490, 2001.
Smid et al., Quantitative Analysis of Fetal DNA in Maternal Plasma in Pathological Conditions Associated with Placental Abnormalities, Annals New York Academy of Sciences, 951:13 3-137, 2001.

(56) References Cited

OTHER PUBLICATIONS

Gonzalez, et al., Application of Fetal DNA Detection in Maternal Plasma: A Prenatal Diagnosis Unit Experience, Journal of Histochemistry & Cytochemistry, 53(3): 307-314, 2005.
Pan, et al., Cell-free Fetal DNA Levels in Pregnancies Conceived by IVF, Human Reproduction, 20(11):3132-3156, 2003.
Takabayashi, et al., Development of Non-invasive Fetal DNA Diagnosis from Maternal Blood, Prenatal Diagnosis, 15:74-77, 1995.
Yi Zhang, et al., Effect of Formaldehyde Treatment on the Recovery of Cell-Free Fetal DNA from Maternal Plasma at Different Processing Times Clinica Chimica Acta 397 (2008) 60-64.
Ravinder Dhallan, MD, PhD, et al., Methods to Increase the Percentage of Free Fetal DNA Recovered from the Maternal Ciculation, JAMA 291 (2004) 1114-1119.
YM Dennis Lo, et al., Presence of Fetal DNA in Maternal Plasma and Serum, Lancet 350 (1997) 485-87.
Technical Briefs—"Treatment of Material Blood Samples with Formaldehyde does not alter the Proportion of Circulatory Fetal Nucleic Acids (DNA and MRNA) in Material Plasma", University Women's Hospital/Dept. of Research, Basel, Switzerland, pp. 652-655; 2005.
Detrimental Effect of Formaldehyde on Plasma RNA Detection; Chung et al. 51 (6): 10; 2005.
Technical Briefs, "Evaluation of Different Approaches for Fetal DNA Analysis from Maternal Plasma and Nucleated Blood Cells", pp. 1570-1572; 1999.
Circulating Nucleic Acids in Plasma and Serum; An Overview, Y.M., Dennis Lo; 2001.
European Office Action dated Mar. 12, 2014; Appln. No. 13166264.5.
Sigma-Aldrich. "J-Aza-3,7-dioxabicyclo[3.3.0]octane-5-methanol solution," Available onnline at www.sigmaaldrich.com/catalog/product/aldrich/417807?lang=en&region=US. 5 pages. Accessed Jan. 13, 2014.
Extended Search Report for Appln. 13166264.5 dated Jul. 16, 2013.
Lo Y M Dennis et al., "Noninvasive prenatal diagnosis of fetal chromosomal aneuploidies by maternal plasma nucleic acid analysis" Clinical Chemistry, American Association for Clinical Chemistry, Washington, DC LNKD—DOI:10.1373/CLINCHEM.2007.100016, vol. 54, No. 3, Jan. 17, 2008, pp. 461-466.
European Office Action dated Oct. 14, 2014; Appln. No. 10000518.0.
Ashoor G, Syngelaki A, Wang E, Struble C, Oliphant A, Song K, Nicolaides KH. Trisomy 13 detection in the first trimester of pregnancy using a chromosome-selective cell-free DNA analysis method. Ultrasound in Obstetrics & Gynecolgy. Jan. 1, 2013;41(1):21-5.
Barrett AN, Zimmermann BG, Wang D, Holloway A, Chitty LS. Implementing prenatal diagnosis based on cell-free fetal DNA: accurate identification of factors affecting fetal DNA yield. PLoS One. Oct. 4, 2011;6(10):e25202.
Baylndir B, Dehaspe L, Brison N, Brady P, Ardul S, Kammoun M, Van der Veken L, Lichtenbelt K, Van den Bogaert K, Van Houdt J, Peeters H. Noninvasive prenatal testing using a novel analysis pipeline to screen for all autosomal fetal aneuploidies improves pregnancy management. European Journal of Human Genetics. Jan. 14, 2015.
Beck J, Bierau S, Balzer S, Andag R, Kanzow P, Schmitz J, Gaedcke J, Moerer O, Slotta JE, Walson P, Kollmar O, Digital droplet PCR for rapid quantification of donor DNA in the circulation of transplant recipients as a potential universal biomarker of graft injury. Clinical chemistry. Dec. 1, 2013;59(12):1732-41.
Benachi A, Letoumeau A, Kleinfinger P, Senat MV, Gautier E, Favre R, Bidat L, Houfflin-Debarge V, Bouyer J, Costa JM. Cell-Free DNA Analysis in Maternal Plasma in Cases of Fetal Abnormalities Detected on Ultrasound Examination. Obstetrics & Gynecology. Jun. 1, 2915;125(6):1330-7.
Bevilacqua E, Gil MM, Nicolaides KH, Ordoñez E, Cirigliano V, Dierickx H, Willems PJ, Jani JC. Performance of screening for aneuploidies by cell-free DNA analysis of maternal blood in twin pregnancies. Ultrasound in Obstetrics & Gynecolgy. Jan. 1, 2015;45(1):61-6.
Bethel K, Luttgen MS, Damani S, Kolatkar A, Lamy R, Sabouri-Ghomi M, Topol S, Topol EJ, Kuhn P. Fluid phase biopsy for detection and characterization of circulating endothelial cells in myocardial infarction. Physical biology. Feb. 1, 2014;11(1):018002.
Bianchi DW, Parker RL, Wentworth J, Madankumar R, Saffer C, Das AF, Craig JA, Chudova DI, Devers PL, Jones KW, Oliver K. DNA sequencing versus standard prenatal aneuploidy screening. New England Journal of Medicine, Feb. 27, 2014;370(9):799-808.
Bianchi DW, Parsa S, Bhatt S. Halks-Miller M, Kurtzman K, Sehnert AJ, Swanson A. Fetal sex chromosome testing by maternal plasma DNA sequencing: clinical laboratory experience and biology. Obstetrics & Gynecology. Feb. 1, 2015;125(2):375-82.
Brar H, Wang E, Struble C, Musci TJ, Norton ME. The fetal fraction of cell-free DNA in maternal plasma is not affected by a priori risk of fetal trisomy. The Journal of Maternal-Fetal & Neonatal Medicine. Jan. 1, 2013;26(2):143-5.
Bruno DL, Ganesamoorthy O, Thorne NP, Ling L, Bahlo M, Forrest S, Veenendaal M, Katerelos M, Skene A, Ierino FL, Power DA. Use of copy number deletion polymorphisms to assess DNA chimerism. Clinical chemistry. Aug. 1, 2014;50(8):1105-14.
Buysse K, Beulen L, Gomes I, Gilissen C, Keesmaat C, Janssen IM, Derks-Willemen JJ, de Ligt J, Feenstra I, Bekker MN, van Vugt JM. Reliable noninvasive prenatal testing by massively parallel sequencing of circulating cell-free DNA from maternal plasma processed up to 24h after venipuncture. Clinical biochemistry. Dec. 31, 2013;46(18):1783-6.
Carlsson A, Nair VS, Luttgen MS, Keu KV, Horng G, Vasanawala M, Kolatkar A, Jarnali M, Iagaru AH, Kuschner W, Loo Jr BW. Circulating Tumor Microemboli Diagnostics for Patients with Non-Small-Cell Lung Cancer. Journal of Thoracic Oncology. Aug. 1, 2014;9(8):1111-9.
Chudziak J, Burt DJ, Mohan S, Rothwell DG, Mesquita B, Antonello J, Dalby S, Ayub M, Priest L, Carter L, Krebs MG. Clinical evaluation of a novel microfluidic device for epitope-independent enrichment of ciculating tumour cells in patients with small cell lung cancer. Analyst, 2016;141(2):669-78.
Clark-Ganheart CA, Fries MH, Leifheit KM, Jensen TJ, Moreno-Ruiz NL, Peggy PY, Jennings JM, Driggers RW. Use of Cell-Free DNA in the Investigation of Intrauterine Fetal Demise and Miscarriage. Obstetrics & Gynecology. Jun. 1, 2015;125(6):1321-9.
Comas C, Echevarria M, Rodriguez MA, Prats P, Rodriguez I, Serra B. Initial experience with non-invasive prenatal testing of cell-free DNA for major chromosomal anomalies in a clinical setting. The Journal of Maternal-Fetal & Neonatal Medicine, Aug. 12 2014(0):1-6.
Curnow KJ, Wilkins-Haug L, Ryan A, Kirkizlar E, Stosic M, Hall MP, Sigurjonsson S, Demko Z, Rabinowitz M, Gross SJ. Detection of triploid, molar, and vanishing twin pregnancies by a single-nucleotide polymorphism—based noninvasive prenatal test. American journal of obstetrics and gynecology. Jan. 31, 2016;212(1):79-e1.
Dash P, Puri RD, Kotecha U, Bijarnia S, Lall M, Verma IC. Using Noninvasive Prenatal Testing for Aneuploidies in a Developing Country: Lessons Learnt, Journal of Fetal Medicine. 2014;1(3):131-5.
Denis MG, Knol AC, Théoleyre S, Vallée A, Dréno B. Efficient Detection of BRAF Mutation in Plasma of Patients after Long-term Storage of Blood in Cell-Free DNA Blood Collection Tubes. Clinical chemistry. Jun. 1, 2015;61(6):856-8.
Dherajiya N, Zwiefelhofer T, Guan X, Angkachatchai V, Saldivar JS. Noninvasive Prenatal Testing Using Cell-Free Fetal DNA in Maternal Plasma. Current Protocols in Human Genetics. Jan. 20, 2015:8-15.
Diamond EL, Durham BH, Haroche J, Yao Z, Ma J, Parikh SA, Wang Z, Choi J, Kim E, Cohen-Aubart F, Lee SC. Diverse and Targetable Kinase Alterations Drive Histiocytic Neoplasms. Cancer discovery. Nov. 13, 2015:CD-15.

(56) References Cited

OTHER PUBLICATIONS

Fairbrother G, Johnson S, Musci TJ, Song K. Clinical experience of noninvasive prenatal testing with cell-free DNA for fetal trisomies 21, 18, and 13, in a general screening population. Prenatal diagnosis. Jun. 1, 2013;33(6):580-3.

Futch T, Spinosa J, Bhatt S, Feo E, Rava RP, Sehnert AJ. Initial clinical laboratory experience in noninvasive prenatal testing for fetal aneuploidy from maternal plasma DNA samples. Prenatal diagnosis. Jun. 1, 2013:33(6):569-74.

Gil MD, Quezada MS, Bregant B, Syngelaki A, Nicolaides KH. Cell-free DNA analysis for trisomy risk assessment in first-trimester twin pregnancies. Fetal diagnosis and therapy. Nov. 15, 2013;35(3):204-11.

Gil MM, Giunta G, Macelli EA, Poon LC, Nicolaides KH. UK NHS pilot study on cell-free DNA testing in screening for fetal trisomies: factors affecting uptake. Ultrasound in Obstetrics & Gynecology. Jan. 1, 2015;45(1):67-73.

Gil MM, Quezada MS, Bregant B, Ferraro M, Nicolaides KH. Implementation of maternal blood cell-free DNA testing in early screening for aneuploidies. Ultrasound in Obstetrics & Gynecology. Jul. 1, 2013;42(1):34-40.

Grömminger S, Yagmur E, Erkan S, Nagy S, Schöck U, Bonnet J, Smerdka P, Enrich M, Wegner RD, Hofmann W, Stumm M. Fetal aneuploidy detection by cell-free DNA sequencing for multiple pregnancies and quality issues with vanishing twins. Journal of Clinical Medicine. Jun. 25, 2014;3(3):679-92.

Gross ME, Dorff TB, Quinn DI, Agus DB, Luttgen M, Bethel K, Kolatkar A, Kuhn P. Rapid changes in circulating tumor cells following anti-angiogenic therapy. Convergent Science Physical Oncology. Sep. 10, 2015;1(1):015002.

Hidestrand M, Stokowski R, Song K, Oliphant A, Deavers J, Goetsch M, Simpson P, Kuhlman R, Ames M, Mitchell M, Tomita-Mitchell A. Influence of temperature during transportation on cell-free DNA analysis. Fetal diagnosis and therapy. 2012;31(2):122-8.

Hindson BJ, Ness KD, Masquelier DA, Belgrader P, Heredia NJ, Makarewicz AJ, Bright IJ, Lucero MY, Hiddessen AL, Legler TC, Kitano TK. High-throughput droplet digital PCR system for absolute quantitation of DNA copy number. Analytical chemistry. Oct. 28, 2011;83(22):8604-10.

Holmberg RC, Gindlesperger A, Stokes T, Lopez D, Hyman L, Freed M, Belgrader P, Harvey J, Li Z. Akonni TruTip® and Qlagen® methods for extraction of fetal circulating DNA—evaluation by real-time and digital PCR. PloS One. Aug. 1, 2013;8(8):e73068.

Hooks J, Wolfberg AJ, Wang ET, Struble CA, Zahn J, Juneau K, Mohseni M, Huang S, Bogard P, Song K, Oliphant A. Non-invasive risk assessment of fetal sex chromosome aneuploidy through directed analysis and incorporation of fetal fraction. Prenatal diagnosis. May 1, 2014;34(5):49-9.

Hynek M, Zembol F, Putzová M, Marešová I, Horácková S, Zvárová J, Stejskal D. MoM-based Approach to Noninvasive Prenatal Testing Using Exponentially Weighted Moving Average Chart and Chromosomal Fingerprint. International Journal of Biomedicine and Healthcare:12, 2015.

Ignatiadis M, Lee M, Jeffrey SS. Circulating Tumor Cells and Circulating Tumor DNA: Challenges and Opportunities on the Path to Clinical Utility. Clinical Cancer Research. Nov. 1, 2015;21(21):4786-800.

Jensen TJ, Zwiefelhofer T, Tim RC, Dzakula Z, Kim SK, Mazloorn AR, Zhu Z, Tynan J, Lu T, McLennan G, Palornaki GE. High-throughput massively parallel sequencing for fetal aneuploidy detection from maternal plasma. PloS One. Mar. 1, 2013;8(3):e57381.

Jeon YJ, Zhou Y, Li Y, Guo Q, Chen J, Quan S, Zhang A, Zheng H, Zhu X, Lin J, Xu H. The feasibility study of non-invasive fetal trisomy 18 and 21 detection with semiconductor sequencing platform. PLoS One, Oct. 20, 2014;9(10):e110240.

Juneau K, Bogard PE, Huang S, Mohseni M, Wang ET, Ryvkin P, Kingsley C, Struble CA, Oliphant A, Zahn JM. Microarray-based cell-free DNA analysis improves noninvasive prenatal testing. Fetal diagnosis and therapy. 2014;36(4):282-6.

Kadam SK, Farmer M, Brandt JT. Quantitative measurement of cell-free plasma DNA and applications for detecting tumor genetic variation and promoter methylation in a clinical setting. The Journal of Molecular Diagnostics. Jul. 31, 2012;14(4):346-56.

Kidess E, Heirich K, Wiggin M, Vysotskaia V, Visser BC, Merziali A, Wiedenmann B, Norton JA, Lee M, Jeffrey SS, Poultsides GA. Mutation profiling of tumor DNA from plasma and tumor tissue of colorectal cancer patients with a novel, high-sensitivity multiplexed mutation detection platform. Oncotarget. Feb. 2015;6(4):2549.

Kirkizlar E, Zimmermann B, Constantin T, Swenerton R, Hoang B, Wayham N, Babiarz JE, Demko Z, Pelham RJ, Kareht S, Simon AL. Detection of Clonal and Subclonal Copy-Number Variants in Cell-Free DNA from Patients with Breast Cancer Using a Massively Multiplexed PCR Methodology. Translational oncolocgy. Oct. 31, 2015;8(5):407-16.

Kwee S, Song M, Cheng I, Loo L, Tiirikainen M. Measurement of Circulating Cell-Free DNA in Relation to 18F-Fluorocholine PET/CT Imaging in Chemotherapy—Treated Advanced Prostate Cancer. Clinical and translational science. Feb. 1, 2012;5(1):65-70.

Lambert-Messerlian GM, Palomaki GE, Eklund EE, Kioza EM, Neveux LM, Phipps MG, Canick JA. Feasibility of using plasma rather than serum in first and second trimester multiple marker Down's syndrome screening. Journal of medical screening. Dec. 1, 2012;19(4):164-70.

Leman RB, Mortimer SA, Zill OA, Sebisanovic D, Lopez R, Blau S, Collisson EA, Divers SG, Hoon DS, Kopetz ES, Lee J. Analytical and clinical validation of a digital sequencing panel for quantitative, highly accurate evaluation of cell-free circulating tumor DNA. PloS one. Oct. 16, 2015;10(10):e0140712.

Lee MY, Cho DY, Won HS, Hwang AR, Jeong B, Kim J, Oh M. Performance of Momguard, a new non-invasive prenatal testing protocol developed in Korea. Obstetrics & gynecology science. Sep. 1, 2015;58(5):340-5.

Liao C, Yin AH, Peng CF, Fu F, Yang JX, Li R, Chen YY, Luo DH, Zhang YL, Ou YM, Li J. Noninvasive prenatal diagnosis of common aneuploidies by semiconductor sequencing. Proceedings of the National Academy of Sciences. May 20, 2014;111(20):7415-20.

Liu XY, Zhang HG, Wang RX, Chen S, Yu XW, Liu RZ. Placental mosaicism for Trisomy 13: a challenge in providing the cell-free, fetal DNA testing. Journal of assisted reproduction and genetics. May 1, 2014;31(5):589-94.

Lu D, Graf RP, Harvey M, Madan RA, Heery C, Marte J, Beasley S, Tsang KY, Krupa R, Louw J, Wahl J. Detection and Characterization of Circulating Tumour Cells from Frozen Peripheral Blood Mononuclear Cells. Journal of Circulating Biomarkers. Dec. 1, 2015;35(12):1243-6.

McCullough RM, Almasri EA, Guan X, Geis JA, Hicks SC, Mazloom AR, Deciu C, Oeth P, Bombard AT, Paxton B, Dharajiya N, Salidivar JS. Non-invasive prenatal chromosomal aneuploidy testing-clinical experience: 100,000 clinical samples. PLoS One. Oct. 7, 2014;9(10):e109173.

Nair VS, Keu KV, Luttgen MS, Kolatkar A, Vasanawala M, Kuschner W, Bethel K, Iagaru AH, Hoh C, Shrager JB, Loo Jr BW. An observational study of circulating tumor cells and (18) F-FDG PET uptake in patients witth treatment-naive non-small cell lung cancer. PloS One. Jul. 5, 2013;8(7):e67733.

Nicolaides KH, Syngelaki A, Gil M, Atanasova V, Markova D. Validation of targeted sequencing of single-nucleotide plymorphisms for non-invasive prenatal detection of aneuploidy of chromosomes 13, 18, 21, X, and Y. Prenatal diagnosis. Jun. 1, 2013;33(6):575-9.

Norton ME, Brar H, Weiss J, Karimi A, Laurent LC, Caughey AB, Rodriguez MH, Williams J, Mitchell ME, Adair CD, Lee H. Non-Invasive Chromosomal Evaluation (NICE) Study: results of a multicenter prospective cohort study for detection of fetal trisomy 21 and trisomy 18. American Journal of Obstetrics and Gynecology. Aug. 31, 2012;207(2):137-e1.

Norton ME, Jacobsson B, Swamy GK, Laurent LC, Rarizini AC, Brar H, Tomlinson MW, Pereira L, Spitz JL, Hollemon D, Cuckle H. Cell-free DNA analysis for noninvasive examination of trisomy. New England Journal of Medicine. Apr. 23, 2015;372(17):1589-97.

(56) References Cited

OTHER PUBLICATIONS

Ono S, Lam S, Nagahara M, Hoon DS. Circulating microRNA Biomarkers as Liquid Biopsy for Cancer Patients: Pros and Cons of Current Assays. Journal of clinical medicine. Oct. 23, 2015;4(10):1890-907.
Persico N, Boito S, Ischia B, Cordisco A, De Robertis V, Fabietti I, Periti E, Volpe P, Fedele L, Rembouskos G. Cell-free DNA testing in the maternal blood inn high-risk pregnancies after first trimester combined screening. Prenatal Diagnosis. Jan. 1, 2016.
Punnoose EA, Ferraldeschi R, Szafer-Glusman E, Tucker EK, Mohan S, Flohr P, Riisnaes R, Miranda S, Figueiredo I, Rodrigues DN, Omlin A. PTEN loss in circulating tumour cells correlates with PTEN loss in fresh tumour tissue from castration-resistant prostate cancer patients. British Journal of Cancer. Oct. 20, 2015;113(8):1225-33.
Quezada MS, Gil MM, Francisco C, Orósz G, Nicolaides KH. Screening for trisomies 21, 18 and 13 by cell-free DNA analysis of maternal blood at 10-11 weeks' gestation and the combined test at 11-13 weeks. Ultrasound in Obstetrics & Gynecology. Jan. 1, 2015;45(1):36-41.
Quezada MS, Francisco C, Dumitrascu-Biris D, Nicolaides KH, Poon LC. Fetal fraction of cell-free DNA in maternal plasma in the prediction of spontaneous preterm delivery. Ultrasound in Obstetrics & Gynecology. Jan. 1, 2015;45(1):101-5.
Risberg B. Establishment of PCR based methods for detection of ctDNA in blood. Thesis submitted for the Master's degree in Biomedicine. Oslo University Hospital, Institute for Cancer Research, Department of Genetics and Oslo and Akerrshus University College of Applied Sciences. May 5, 2013.
Ruiz C, Li J, Luttgen MS, Kolatkar A, Kendall JT, Flores E, Topp Z, Samlowski WE, McClay E, Bethel K, Ferrone S. Limited genomic heterogeneity of circulating melanoma cells in advanced stage patients. Physical biology. Feb 1, 2015;12(1):016008.
Salvianti F, Pazzagli M, Pinzani P. Single circulating tumor cell sequencing as an advanced tool in cancer management. Expert review of molecular diagnostics. Nov . 27, 2015:1-3.
Samango-Sprouse C, Banjevic M, Ryan A, Siguriorisson S, Zimmermann B, Hill M, Hall MP, Westemeyer M, Saucier J, Demko Z, Rabinowitz M. SNP-based non-invasive prenatal testing detects sex chromosome aneuploidies with high accuracy. Prenatal diagnosis. Jul. 1, 2013;33(7):643-9.
Samolla A, Patel C, Kothadia KJ, You D, Lemetre C, Scacalossi DM, Babady NE, Peerschke EI. Method development and validation for clinical cfDNA extraction from blood, InASCO Annual Meeting Proceedings May 20, 2015 (vol. 33, No. 15_suppl. p. e22185).
Samuel AR, Son M, Ananth CV, Wapner RJ. The effect of chorionic villus sampling on the fraction of cell-free fetal DNA in maternal plasma. The Journal of Maternal-Fetal & Neonatal Medicine. Oct. 15, 2015:1-4.
Schaffer PG, Van Der School, CE, Page-Christiaens GC, De Haas M. Noninvasive fetal blood group genotyping of rhesus D, c, E and of K in alloimmunised pregnant women: evaluation of a 7-year clinical experience.BJOG: an International Journal of Obstetrics & Gynaecology. Oct. 1, 2011;118(11):1340-8.
Schiavon G, Hrebien S, Garcia-Murillas I, Cutts RJ, Pearson A, Tarazona N, Fenwick K, Kozarewa I, Lopez-Knowles E, Ribas R, Nerurkar A. Analysis of ESR1 mutation in circulating tumor DNA demonstrates evolution during therapy for metastatic breast cancer. Science translational medicine. Nov. 11, 2015;7(313):313ra182-.
Seo DH, Cho SE, Kwak JR. An Experience of Using the Harmony Test for Genomics-Based Non-Invasive Prenatal Testing. Journal of Laboratory Medicine and Quality Assurance. Mar. 1, 2015;37(1):44-6.
Shi X, Zhang Z, Cram DS, Liu C. Feasibility of noninvasive prenatal testing for common fetal aneuploidies in an early gestational window. Clinica Chimica Acta. Jan. 15, 2015;439:24-8.
Sallence KA, Roberts LA, Hollands HJ, Thompson HP, Kiernan M, Madgett TE, Welch CR, Avent ND. Fetal Sex and RHD Genotyping with Digital PCR Demonstrates Greater Sensitivity than Real-time PCR. Clinical chemistry. Nov. 1, 2015;61(11):1399-407.
Song Y, Huang S, Zhou X, Jiang Y, Qi Q, Bian X, Zhang J, Yan Y, Cram DS, Liu J. Non-invasive prenatal testing for fetal aneuploidies in the first trimester of pregnancy. Ultrasound in Obstetrics & Gynecology. Jan. 1, 2015;45(1):55-60.
Sparks AB, Struble CA, Wang ET, Song K, Oliphant A. Noninvasive prenatal detection and selective analysis of cell free DNA obtained from maternal blood: evaluation for trisomy 21 and trisomy 18. American journal of obstetrics and gynecology. Apr. 30, 2012;206(4):319-e1.
Sparks AB, Wang ET, Struble CA, Barrett W, Stokowski R, McBride C, Zahn J, Lee K, Shen N, Doshi J, Sun M. Selective analysis of cell-free DNA in maternal blood for evaluation of fetal trisomy. Prenatal diagnosis. Jan. 1, 2012;32(1):3-9.
Stokowski R, Wang E, White K, Batey A, Jacobsson B, Brar H, Balanarasimha M, Hollemon D, Sparks A, Nicolaides K, Musci TJ. Clinical performance of non-invasive prenatal testing (NIPT) using targeted cell-free DNA analysis in maternal plasma with microarrays or next generation sequencing (NGS) is consistent across multiple controlled clinical studies. Prenatal diagnosis. Dec. 1, 2015;35(12):1243-6.
Stumm M, Entezami M, Haug K, Blank C, Wüstemann M, Schulze B, Raabe-Meyer G, Hempel M, Schelling M, Ostermayer E, Langer-Freitag S. Diagnostic accuracy of random massively parallel sequencing for non-invasive prenatal detection of common autosomal aneuploidies: a collaborative study in Europe. Prenatal diagnosis. Feb. 1, 2014;34(2):185-91.
Thung DT, Beulen L, Hehir-Kwa J, Faas BH. Implementation of whole genome massively parallel sequencing for noninvasive prenatal testing in laboratories. Expert review of molecular diagnostics. Jan. 2, 2015;15(1):111-24.
Toro PLV. Detection of PIK3CA Mutations in Plasma Tumor DNA Circulating in Peripheral Blood of Breast Cancer Patients. Thesis submitted for the degree of Master of Science in Molecular and Cellular Biology. Johns Hopkins University, Baltimore, Maryland. Apr. 2014.
Toro PV, Erlanger B, Beaver JA, Cochran RL, VanDenBerg DA, Yakim E, Cravero K, Chu D, Zabransky DJ, Wong HY, Croessmann S. Comparison of cell stabilizing blood collection tubes for circulating plasma tumor DNA. Clinical biochemistry. Oct. 31, 2015;48(15):993-8.
Tynan JA, Kim SK, Mazloom AR, Zhao C, McLennan G, Tim R, Liu L, Hannum G, Hull A, Bombard AT, Oeth P. Application of risk score analysis to low-coverage whole genome sequencing data for the noninvasive detection of trisomy 21, trisomy 18, and trisomy 13. Prenatal diagnosis. Jan. 1, 2015.
Vandenberghe P, Wlodarska I, Tousseyn T, Dehaspe L, Dierickx D, Verheecke M, Uyttebroeck A, Bechter O, Delforge M, Vandecaveye V, Brison N. Non-invasive detection of genomic imbalances in Hodgkin/Reed-Sternberg cells in early and advanced stage Hodgkin's lymphoma by sequencing of circulating cell-free DNA: a technical proof-of-principle study. The Lancet Haematology. Feb. 28, 2015;2(2):e55-65.
Verweij EJ, Jacobsson B, Scheltema PA, Boer MA, Hoffer MJ, Hollemon D, Westgren M, Song K, Oepkes D. European Non-Invasive Trisomy Evaluation (EU-NITE) study: a multicenter prospective cohort study for non-invasive fetal trisomy 21 testing. Prenatal diagnosis. Oct. 1, 2013;33(10):996-1001.
Wang D, Liu X, Hsieh B, Bruce R, Somlo G, Huang J, Sambucetti L. Exploring Glycan Markers for Immunotyping and Precision-targeting of Breast Circulating Tumor Cells. Archives of medical research. Dec. 1, 2015.
iWang E, Batey A, Struble C, Musci T, Song K, Oliphant A. Gestational age and maternal weight effects on fetal cell-free DNA in maternal plasma. Prenatal diagnosis. Jul. 1, 2013;33(7):662-6.
Wang P, Bahreini A, Gyanchandani R, Lucas P, Hartmaier RJ, Watters RJ, Jonnalagadda AR, Bitter HE, Berg A, Hamilton RL, Kurland BF. Sensitive detection of mono-and polyclonal ESR1 mutations in primary tumors, metastatic lesions and cell free DNA of breast cancer patients. Clinical Cancer Research. Oct. 23, 2015:clincares-1534.

(56) References Cited

OTHER PUBLICATIONS

Wang Q, Cal Y, Brady P, Vermeesch JR. Real-time PCR evaluation of cell-free DNA subjected to various storage and shipping conditions. Genetics and Molecular Research. Jan. 1, 2015;14(4):12797-804.
Wang Y, Cheri Y, Tian F, Zhang J, Song Z, Wu Y, Han X, Hu W, Ma D, Cram D, Cheng W. Maternal mosaicism is a significant contributor to discordant sex chromosomal aneuploidies associated with noninvasive prenatal testing. Clinical chemistry. Jan. 1, 2014;60(1):251-9.
Werner SL, Graf RP, Landers M, Valenta DT, Schroeder M, Greene SB, Bales N, Dittamore R, Marrinucci D. Analytical Validation and Capabilities of the Epic CTC Platform: Enrichment-Free Circulating Tumour Cell Detection and Characterization. Journal of Circulating Biomarkers. 2015 4:3.
Wienzek-Lischke S, Krautwurst A, Fröhner V, Hackstein H, Gattenlöhner S, Bräuninger A, Axt-Fliedner R, Degenhardt J, Deisting C, Santoso S, Sachs UJ. Noninvasive fetal genotyping of human platelet antigen-1a using targeted massively parallel sequencing. Transfusion. Apr. 1, 2015.
Willems PJ, Dlerickx H, Vandenakker ES, Bekedam D, Segers N, Deboulle K, Vereecken A. The first 3,000 non-invasive prenatal tests (NIPT) with the harmony test in Belgium and the Netherlands. Facts, views & vision in ObGyn. 2014;6(1):7.
Wong D, Moturi S, Angkachatchai V, Mueller R, DeSantis G, van den Boom D, Ehrich M. Optimizing blood collection, transport and storage conditions for cell free DNA increases access to prenatal testing. Clinical biochemistry. Aug. 31, 2013;46(12):1009-104.
Woolcock J, Grivell R. Noninvasive prenatal testing. Australian family physician. Jul. 1, 2014;43(7):432.
Zill OA, Greene C, Sebisanovic D, Siew LM, Leng J, Vu M, Hendifar AE, Wang Z, Atreya CE, Kelley RK, Van Loon K. Cell-free DNA next-generation sequencing in pancreatobiliary carcinomas. Cancer discovery. Oct. 1, 2015;5(10):1040-8.
Wiebe, Article in Life Sciences dated Feb. 1991, "Inhibition of Cell Proliferation by Glycerol".
American Association for Cancer Research; 93rd Annual Meeting; Apr. 6-10, 2002; San Francisco, California; vol. 43, Mar. 2002.
Biocept—Expands Patent Protection for Liquid Biopsy Platform dated Jun. 1, 2015; http://ir.biocept.com/releasedetail.cfm?releaseID=915635.
Biocept (BIOC) Announces Patent for Blood Collection and Transport Tube StreetInsider.com; http://www.streetinsider.com/corporate+news/biocept+(BIOC)+Announces; Jun. 1, 2015.
Bioreceptor Ferro fluids: Novel Characteristics and their Utility in Medical Applications; P. A. Liberti, J. N. Chiarappa, A. C. Hovespian, C. G. Rao; Supplied by the British Library; 1996 Kluwer Academic Publishers.
Brown "Effect of Blood Collection and Processing on Radioimmunoassay Results for Apolipoprotein B in Plasma" Clinical Chemistry, 36/9, 1662-1666, 1990.
Butler "Genetics and Genomics of Core Short Tandem Repeat Loci Used in Human Identity Testing," Journal of Forensic Science, vol. 51, No. 2, pp. 253-265, Mar. 2006.
Clinical Applications of Flow Cytometry: Immunophenotyping of Leukemic Cells; Approved Guideline; Jun. 1998; vol. 18 No. 8; NCCLS.
Costa et al. "Fetal Expressed Gene Analysis in maternal Blood: a New Tool for Noninvasive Study of the Fetus" Clinical Chemistry, vol. 49, No. 6, pp. 981-983, 2003.
Fernando et al., "Stabilization of cell-free RNA in blood samples using a new collection device" Clinical Biochemistry, vol. 45, No. 16-17, pp. 1497-1502, dated Nov. 1, 2012.
Gielis, E.M.," Cell-Free DNA: an Upcoming Biomarker in Transplantation," American Journal of Transplantation May 13, 2015. http://ir.biocept.com/secfiling.cfm?filingid=1193125-15-16425&cik=1044378; Biocept Completing the Answer; Jan. 21, 2015.
Kagan et al"A Sample Preparation and Analysis System for Indentification of Circulating Tumor Cells"; vol. 25, No. 1; Spring 2002; Journal of Clinical Ligand Assay.
Kashiwasaki et al. "Influence of upper and lower thermoneitral room temperatures (20° C. and 25° C.) on fasting and post-prandial resting metabolism under different outdoor temperatures," European Journal of Clinical Nutrition, vol. 44, pp. 405-413, 1990.
Katz et al. No Date. "Mass-Volume Equivalents of Common Chemical Solids." Available at <http://www.chymist.com/Mass-volume%20equivalents.pdf>. Accessed Oct. 22, 2015. 4 pages.
Kreuzer et al. "Highly Sensitive and specific Fluorescence Reverse Transcription-PCR Assay for the Psuedogene-free Detection of β-actin Transcripts as Quantitative Reference" Clinical Chemistry, vol. 45, No. 2, pp. 297-300, 1999.
May et al. "How Many Species Are There on Earth?," Science vol. 241 p. 1441-1449, 1988.
Miller "A Simple Salting Out Procedure for Extracting DNA from Human Nucleated Cells," Nucleic Acids Research vol. 16, p. 1215 (1988).
Modrek "Genome-wide Detection of Alternative Splicing in Expressed Sequences of Human Genes," Nucleic Acid Research, vol. 29, No. 13 pp. 2850-2859, (2001).
Rait et al. "Conversions of formaldehyde-modified 2'-deoxyadenosine 5'-monophosphate in conditions modeling formalin-fixed tissue dehydration" J. Histochem Cytochem 54(3): 301-10 (Mar. 1, 2006).
Schatz et al.; "Preservation of Cell-Free DNA in Stored Blood Samples for the Analysis of the (M) Sept9 Colorectal Cancer Screening Marker Enables Sample Shipment by Mail", May 2011, Published as a poser at the conference on International federation of clinical chemistry and laboratory medicine Worldlab and EU, Berlin, Germany.
Skidmore et al., "Characterization and Use of the Potent Ribonuclease Inhibitor Aurintricarboxylic Acid for the Isolation of RNA from Animal Tissues," Biochem Journal, 263, pp. 73-80 (1989).
Slocum et al., "Electron-Microscopic Cytochemical Localization of Diamine and polyamine oxidases in Pea and Maize Tissues," Planta vol. 183, pp. 443-450, (1991).
The Scientific Committee on Cosmetic Product and Non-Food Products intended for Consumers "Opinion Concerning the Determination of Certain Formaldehyde Releasers in Cosmetic Products" Dec. 22, 2002, pp. 1-9.
Wagner "Free DNA—new potential analyte in clinical laboratory diagnostics" Biochem Med (Zagreb) 22(1): 24-38 (2012).
Passage from confidential document, Streck, Inc. Cell-Free DNA BCT 510(k) Premarket Notification, Sep. 19, 2012.
Communication of a notice of opposition including exhibits. EP Application No. 10000518.0 (Patent No. EP2228453) dated Sep. 12, 2017.
Co-Pending U.S. Appl. No. 15/894,077, filed Feb. 12, 2018.
Co-Pending U.S. Appl. No. 15/937,446 filed Mar. 27, 2018.
Office Action from the Canadian Patent Office for Application No. 2,690,651 dated Aug. 31, 2017.
Communication Pursuant to Article 94(3) EPC, Application No. 13166264.5) dated Mar. 9, 2018.
Ames et al, 1975, An Appraisal of the "Vacutainer" System for Blood Collection, Ann. clin. Biochem, 12: 151-155 (Year: 1975).
Merriam-Webster's Medical Dictionary (1995). p. 606. Springfield, MA: Merriam-Webster Incorporated.
Communication of a notice of opposition including exhibits, EP Application No. 13706856.5 (Patent No. EP2814981) dated Apr. 4, 2018.
Communication of a notice of intervention including exhibits by Cenata GmbH, EP Application No. 10000518.0 (Patent No. EP2228453) dated Apr. 13, 2018.
Brief Communication to Opponent 1 and Opponent 2 dated May 29, 2018 and Reply including exhibits of patent proprietor to notice(s) of opposition dated Apr. 26, 2018, EP Application No. 10000518.0 (Patent No. EP2228453).
Brief Communication regarding Letter from the opponent O2 (Cenata) of Jun. 6, 2018 including exhibits, EP Application No. 10000518.0 (Patent No. EP2228453), dated Jun. 14, 2018.
Antje Milde et al.: "Improved DNA typing of human urine by adding EDTA", Int. J Legal Med, Jan. 1, 1999, pp. 209-210, XP055291033.
Botezatu I, Serdyuk OG, Potapova G, Shelepov V, Alechina R, Molyaka Y, Anan'ev V, Bazin I, Garin A, Narimanov M, Knysh V.

(56) References Cited

OTHER PUBLICATIONS

Genetic analysis of DNA excreted in urine: a new approach for detecting specific genomic DNA sequences from cells dying in an organism. Clinical chemistry. Aug. 1, 2000;46(8):1078-84.

Cannas A, Kalunga G, Green C, Calvo L, Katemangwe P, Reither K, Perkins MD, Maboko L, Hoelscher M, Talbot EA, Mwaba P. Implications of storing urinary DNA from different populations for molecular analyses. PloS one. Sep. 10, 2009;4(9):e6985.

Cherepanova A, Tamkovich S, Pyshnyi D, Kharkova M, Vlassov V, Laktionov P. Immunochemical assay for deoxyribonuclease activity in body fluids. Journal of immunological methods. Aug. 31, 2007;325(1):96-103.

Latifa El Bali et al.: "Comparative Study of Seven Commercial Kits for Human DNA Extraction from Urine Samples Suitable for DNA Biomarker-Based Public Health Studies", Journal of Biomolecular Techniques, Dec. 1, 2014.

Nicole T Vu et al.: "Genotyping for DQA1 and PM loci in urine using PCR-based amplification: Effects of sample volume storage temperature, preservatives, and aging on DNA extraction and typing", Forensic Science International., vol. 102, No. 1, May 1, 1999, pp. 23-34.

S.H. Zhang et al.: "Genotyping of urinary samples stored with EDTA for forensic applications", Genetics and Molecular Research, vol. 11, No. 3, May 10, 2012, pp. 3007-3012, XP055291026, DOI: 10.4238/2012.

Su YH, Wang M, Aiamkitsumrit B, Brenner DE, Block TM. Detection of a K-ras mutation in urine of patients with colorectal cancer. Cancer Biomarkers. Jan. 1, 2005;1(2, 3):177-82; abstract only.

Tong YK, Lo YD. Diagnostic developments involving cell-free (circulating) nucleic acids. Clinica Chimica Acta. Jan. 31, 2006;363(1):187-96.

Rykova et al., "Concentrations of Circulating RNA from Healthy Donors and Cancer Patients Estimated by Different Method," Ann. N.Y. Acad. Sci. (2006) vol. 1075, pp. 328-333.

Hallick et al.; Use of Aurintricarboxylic Acid as in Inhibitor of Nucleases During Nucleic Acid Isolation; Nucleic Acid Research, (1977) vol. 4, pp. 3055-3064.

Smit et a; Semiautomated DNA Mutation Analysis Using a Robotic Workstation and Molecular Beacons; Clinical Chemistry, 2001, vol. 47, pp. 739-744.

What are the regulatory Definitions for "Ambient", "Room Temperature" and "Cold Chain" (https://www.gmp-compliance.org/gmp-news/what-are-the-regulatory-defintions-for-ambient-room-temperature-and-cold-chain) 2-3/2017 (036).

Wang and Enkel; Lipoprotient Lipase: from gene to obesity; Am J Physiol Endocrinol Met, 2009, vol. 297, pp. E271-E288.

Canadian Office Action, CA Application No. 2,938,275 dated May 13, 2019.

European Office Action, EP Application No. 13166264.5 dated Jan. 9, 2019.

Ames et al.; 1975, An Appraisal of the "Vacutainer" System for Blood Collection, Ann. Clin. Biochem, 12: 151-155.

Das Kausik et al: "Effects of a novel cell stabilizing reagent on DNA amplification by PCR as compared to traditional stabilizing reagents", Acta Histochemica, vol. 116, No. 1, Jan. 1, 2014.

European Office Action, EP Application No. 20160593.8 dated Jul. 19, 2022.

\* cited by examiner

PRESERVATION OF FETAL NUCLEIC ACIDS IN MATERNAL PLASMA

CLAIM OF PRIORITY

This application claims the benefit of the filing date of U.S. Provisional Application Ser. Nos. 61/146,065, filed on Jan. 21, 2009 and 61/227,529, filed on Jul. 22, 2009, the entirety of the contents of these applications being hereby incorporated by reference for all purposes.

FIELD OF THE INVENTION

This invention relates to prenatal diagnosis of fetal abnormalities and more particularly to the preservation of fetal nucleic acids within a maternal blood sample.

BACKGROUND OF THE INVENTION

The demonstration by Leon et al. in 1977 that cell-free plasma DNA is elevated in cancer patients paved the way for the present day interest in cell-free plasma nucleic acid in disease diagnosis. Relatively recently, Lo et al. *Lancet* 350 (1997) 485-487 have identified the existence of circulating cell-free fetal nucleic acids in maternal plasma. Since this work, a number of studies have demonstrated that cell-free fetal nucleic acids present in maternal plasma can be used in non-invasive prenatal diagnosis.

The analysis of nucleic acids can serve as a predictor of patient vulnerabilities by identifying chromosomes and corresponding genes that represent possible disease-related issues for a patient or a patient's offspring. Research has provided the chromosomal locations of many hereditary diseases and also the genotype or chromosomal mutation that corresponds with the disease. As the genetic markers for these hereditary diseases are ascertained, there is a parallel interest identifying patients that carry these genetic traits, especially when such diseases may only manifest in a patient's offspring. Further, hereditary diseases may only affect a child if both parents carry a necessary allele. In the interest of identifying the offspring that may be stricken with a fatal or debilitating hereditary condition, prenatal testing has become a much more routine practice. However, the difficulty in obtaining the genetic material of a fetus has presented a number of barriers to testing for the many known genetic markers for hereditary disease.

The most thorough and accurate prenatal screening procedures for fetal abnormalities generally involve invasive techniques such as amniocentesis and chorionic villus sampling. While providing reliable results, these procedures are often regarded as carrying a substantial potential risk of pregnancy complications due to their invasive nature. In recent years, the identification of fetal nucleic acids within maternal blood has led to extensive research with a focus on isolating such fetal DNA and RNA to test for any number of fetal abnormalities. Such testing desirably is performed using only a maternal blood sample thereby eliminating the need for the invasive testing procedures. Unfortunately, it has proved challenging to isolate fetal nucleic acids from maternal nucleic acids.

More specifically, in order to obtain consistent and reliable results from the testing of fetal nucleic acids within maternal blood, it is important to both distinguish the fetal nucleic acids from the maternal nucleic acids and to preserve the structural integrity of the fetal nucleic acids. Traditionally, the first step of isolating cell-free nucleic acid from blood is obtaining either serum or plasma and then isolating the cell-free nucleic acids within the serum or plasma. However, serum is generally not suitable for cell-free nucleic acid isolation since blood clotting processes release cellular nucleic acids which contaminate cell-free plasma DNA (see FIG. 1) as well as other deleterious substances that may destabilize the nucleated blood cells. Therefore efforts have been directed also at plasma as preferred starting material for cell-free nucleic acid isolation. Under such an approach, efforts at plasma separation from blood have been carried out to obtain a cell-free plasma sample. Unfortunately, this is frequently a tedious and time consuming multi-step process as it is important to use carefully controlled conditions to prevent cell breakage during centrifugation which will contaminate the cell-free nucleic acids with cellular nucleic acids released during breakage. Another important consideration is that cellular nucleic acid releases into plasma due to cell breakage during ex vivo incubation, typically within a relatively short period of time from a blood draw event. Once maternal cell lysis begins, the lysed maternal cells release additional nucleic acids which become mixed with the cell-free fetal nucleic acids and it becomes increasingly difficult to recover the fetal nucleic acids for testing. Further, the amount and recoverability of available cell-free DNA will decrease substantially over a relatively short period of time due to degradation (e.g., from deoxyribonuclease (DNase) or ribonuclease (RNase) activity) of fetal cell-free DNA (which reduces the already finite supply of fetal DNA that can be recovered for analysis). For example, after a period of about 36 hours, an untreated sample is expected to be sufficiently corrupt that it would not lead to reliable or conclusive analysis. Thus, cell-free nucleic acids desirably are isolated as soon as plasma is separated or the plasma may be frozen at −80° C. until the nucleic acids can be isolated. This too imposes practical constraints upon processing. It would therefore be of great benefit to develop sample processing techniques that would increase the amount of fetal nucleic acids (DNA and/or RNA) recoverable from maternal plasma, making the isolation and testing of the fetal nucleic acids more reliable and consequently improving the diagnostic capabilities of the fetal nucleic acids.

The problems generally associated with the isolation of cell-free nucleic acids include the time consuming and tedious nature of traditional isolation protocols and the requirement that blood samples be processed immediately in an effort to avoid maternal cell lysis. Often, maternal blood samples are immediately treated to remove all maternal cells and the resulting plasma is frozen. However, this process is lengthy and often cell lysis begins before cells are removed. Further, any protocols for removing the maternal cells, including centrifuging the maternal cells out of the sample and plasma freezing may have deleterious effects on the fetal nucleic acids.

In an effort to counter these problems and avoid cell degradation, blood samples have been subjected to a protocol which includes contacting the samples with formaldehyde. Formaldehyde is often used to stabilize cell membranes and its use could therefore reduce maternal cell lysis. Formaldehyde has also been thought to inhibit DNase and RNase thereby increasing the preservation and stability of the cell-free fetal nucleic acids. Studies by Dhallan et al. *JAMA* 291 (2004) 1114-1119 have demonstrated a decrease in cell lysis and a substantial increase in the amount of recoverable cell-free fetal nucleic acids. However, other studies have countered this data indicating that the formaldehyde does not have the desired effect. Most recently, Zhang et al., *Clinical Chimica Acta* 397 (2008) 60-64, determined that the effect of formaldehyde on the percentage of fetal DNA in maternal plasma depends on processing time, wherein formaldehyde has little to no effect on samples processed at 6 hours, but has substantial preservation effect on samples processed at 36 hours. More particularly, samples contacted with formaldehyde and processed at 36 hours were found have reduced cell lysis and increased inhibition of plasma DNase activity. The use of formaldehyde for such purposes is discussed in U.S. Pat. Nos. 7,332,277 and 7,442,506, incorporated by reference herein.

The potential for unreliability and toxicity considerations attendant with formaldehyde processing make its use for maternal plasma preservation undesirable. Given the immense discrepancies regarding the use of formaldehyde for fetal DNA sample preservation, there remains a need for a processing protocol that will consistently reduce one or any combination of maternal cell lysis and DNase and/or RNase activity within maternal plasma samples. It is further desired that such protocol allow for increased sample storage time, so that samples can be taken from a pregnant patient and subsequently stored or sent to a remote location for testing without fear of reduced integrity of the fetal nucleic acids.

A number of patent documents address such processes for the stabilizing, identification and testing of fetal cells and/or nucleic acids located within blood. See, generally, U.S. Pat. Nos. 5,447,842; 5,457,024; 5,861,253; 6,258,540; 6,617,170; 6,821,789; 7,332,277; 7,442,506 and U.S. Patent Publication Nos. 2007/0111233; 2007/0134658; 2007/0202525; 2008/0020390; and 2008/0108071 all incorporated by reference herein. Further, a substantial amount of academic research has been published in regard to fetal cell-free DNA and associated topics.

Notwithstanding the above, there remains a need for fetal nucleic acid isolation and preservation methods that are simplified and less time consuming. It is further desirable that these methods increase the amount of recovered fetal DNA and RNA from maternal plasma (e.g., as compared with methods that do not employ the teachings herein) while maintaining the integrity of the DNA and RNA and producing reliable diagnostic results. Efforts to increase the reliability and consistency of fetal nucleic acid analysis include treating a maternal blood sample so that the amount of viable fetal DNA and/or RNA recovered is increased. The concentration of cell-free fetal DNA found within samples of maternal plasma at the time of blood draw generally ranges from 3.4% to 6.2% of the total amount of the cell-free DNA that is present in the plasma, depending on duration of gestation.

The present invention addresses the need for an efficient and consistent method of preserving and testing fetal nucleic acids from within maternal plasma. By providing an improved method for the reduction of maternal cell lysis and nuclease activity, the present invention includes a protocol that increases the amount of recoverable fetal nucleic acids thereby improving the diagnostic reliability of the fetal nucleic acids. The present invention helps prevent contamination of plasma cell-free nucleic acids with cellular nucleic acids that are released from damaged cells. The present invention further helps to inhibit nuclease activity to protect the integrity of the cell-free plasma nucleic acid. The stabilizing of the nucleated blood cells within a blood sample makes it no longer necessary to separate plasma immediately after blood draw. The present invention may further allow for blood samples to be stored at room temperature for up to about 14 days without compromising the integrity of the cell-free nucleic acids present in the plasma and without contaminating the sample with cellular nucleic acids originating from lysed cells. The present invention may also make it possible to avoid any freezing of the plasma and/or contact with any formaldehyde.

One advantage of the present invention is the possibility for essentially simultaneous stabilizing of both the nucleated blood cells and cell-free nucleic acids. This helps to prevent cellular genomic nucleic acids (e.g., maternal cellular genomic nucleic acids) from being released into plasma, and further diluting the fetal nucleic acids (and associated biomarkers) of interest, while also maintaining the structural integrity of the fetal nucleic acids. An additional possible advantage of the present invention lies in its ability to maintain relative amounts of fetal nucleic acids. In vivo there is constant replenishment of the fetal nucleic acids to maintain a consistent amount of fetal nucleic acids but upon blood draw the fetal nucleic acid amounts will deteriorate without replenishment. The teachings of the present invention also contemplate the possibility to arrest the degradation of the fetal nucleic acids post-blood draw.

SUMMARY OF THE INVENTION

In a first aspect, the present invention contemplates a non-invasive prenatal screening method for the identification of fetal characteristics. The method includes the steps of: contacting a drawn maternal blood sample that includes a plurality of blood cells with a nucleic acid protective agent in an amount and time sufficient so that the blood cells are substantially prevented from (i) releasing genomic nucleic acids into the blood sample and from (ii) experiencing nuclease activity that degrades fetal nucleic acid; isolating fetal nucleic acids from the maternal blood sample; and analyzing the isolated fetal nucleic acids to identify a fetal characteristic.

The nucleic acid protective agent may include a formaldehyde releaser preservative agent such as one selected from the group consisting of: diazolidinyl urea, imidazolidinyl urea, dimethoylol-5,5-dimethylhydantoin, dimethylol urea, 2-bromo-2.-nitropropane-1,3-diol, oxazolidines, sodium hydroxymethyl glycinate, 5-hydroxymethoxymethyl-1-1aza-3,7-dioxabicyclo [3.3.0]octane, 5-hydroxymethyl-1-1aza-3,7dioxabicyclo[3.3.0]octane, 5-hydroxypoly[methyleneoxy]methyl-1-1 aza-3,7dioxabicyclo[3.3.0]octane, quaternary adamantine and any combination thereof. The concentration of the preservative agent prior to the contacting step may be between about 0.1 g/ml and about 3 g/ml. The concentration of the preservative agent prior to the contacting step may be between about 0.4 g/ml and about 0.8 g/ml. The concentration of the preservative agent prior to the contacting step may be a concentration at which cross-linking of nucleic acids and proteins is observed, as indicated by agarose gel electrophoresis. The amount of the preservative agent in a treated sample may be less than about 20 mg/ml of the blood sample.

The isolating step may include isolating nucleic acid from maternal plasma and isolating the fetal nucleic acid in the absence of any cell. Either or both of the isolating or analyzing steps may occur at least 2 hours, 7 days, or even 14 days after the blood sample is drawn. Either or both of the isolating or analyzing steps may occur without and/or prior to any freezing the blood sample or any of its constituents (e.g. to a temperature colder than about −30° C. (more preferably colder than −70° C.)).

The fetal nucleic acid may be DNA, RNA or both. The analyzing step, the isolating step or both may include a step of contacting the fetal nucleic acid with an enzyme, an amplifier or both. The contacting step may take place in a blood collection tube into which the blood sample is drawn (e.g., while the blood sample is entering a blood collection tube). The contacting step may take place as the blood sample is drawn. The contacting step may be sufficient so that after a period of at least 7 days (or even 14 days) from the time the blood sample is drawn, the amount of fetal nucleic acid is at least about 90% of the amount of fetal nucleic acid at the time the blood sample is drawn. The contacting step may be sufficient so that after a period of at least 7 days from the time the blood sample is drawn, the amount of fetal nucleic acid present in the sample is about 100% of the amount of fetal nucleic acid present in the sample at the time the blood sample is drawn. The contacting step may be sufficient so that after a period of at least about 14 days from the time the blood sample is drawn, the concentration of fetal nucleic acid relative to the total nucleic acid in the blood sample that is present is at least about 10 to at least about 50 times the amount of fetal nucleic acid that would be present in the absence of the contacting step.

The protective agent may include a nuclease inhibitor selected from the group consisting of: diethyl pyrocarbonate, ethanol, aurintricarboxylic acid (ATA), formamide, vanadyl-ribonucleoside complexes, macaloid, ethylenediamine tetraacetic acid (EDTA), proteinase K, heparin, hydroxylamine-oxygen-cupric ion, bentonite, ammonium sulfate, dithiothreitol (DTT), beta-mercaptoethanol, cysteine, dithioerythritol, tris(2-carboxyethyl) phosphene hydrochloride, a divalent cation such as $Mg^{+2}$, $Mn^{+2}$, $Zn^{+2}$, $Fe^{+2}$, $Ca^{+2}$, $Cu^{+2}$ and any combination thereof. The protective agent may include an anticoagulant selected from the group consisting of heparin, ethylenediamine tetraacetic acid, citrate, oxalate, and any combination thereof. The protective agent may include a preservative agent and an anticoagulant. The protective agent may include imidazolidinyl urea and ethylenediamine tetraacetic acid.

DETAILED DESCRIPTION

Figure 1:
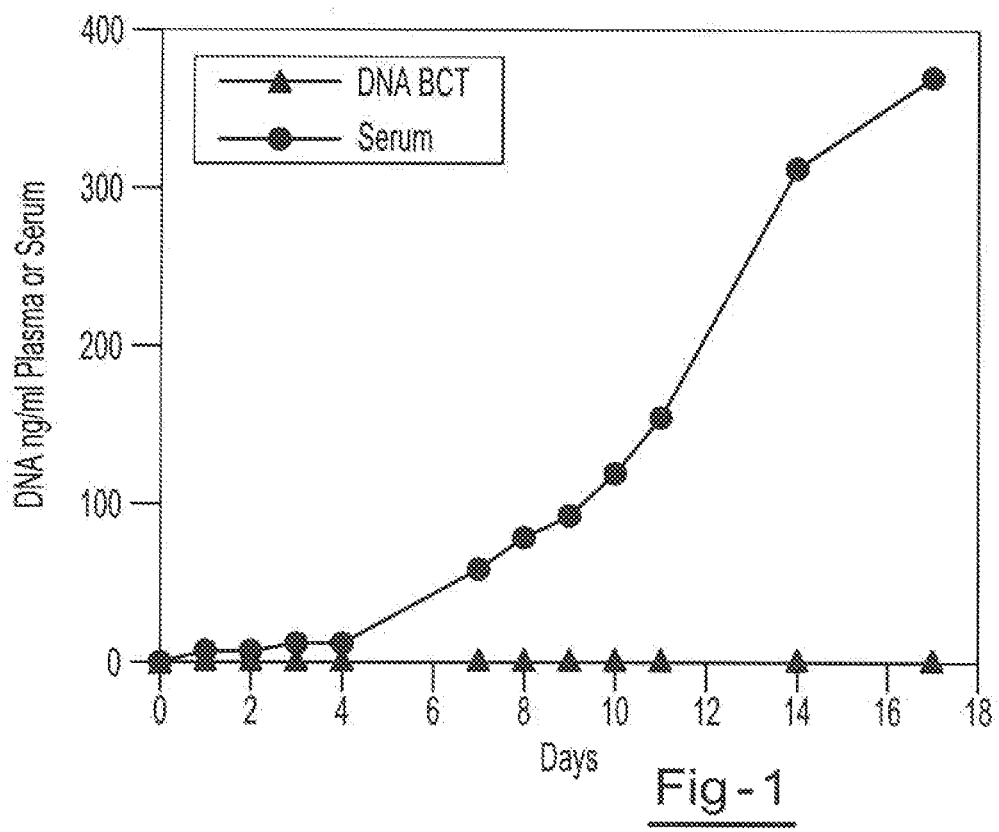
FIG. 1 is an illustrative graphic representation showing the relative amounts of cellular DNA present as a result of cell leakage within two blood samples stored at room temperature over time; there is seen a plot of "DNA BCT" data that extends substantially entirely along the x-axis at a y-axis (0 DNA) value of zero (0).

In general, the invention herein contemplates a method of prenatal screening which includes the isolation and preservation of fetal nucleic acids located within maternal blood. A unique preservation step acts to increase the amount of recoverable fetal nucleic acids thereby improving the diagnostic capabilities of the fetal DNA and RNA.

More particularly, the present invention provides a method for the isolation of fetal nucleic acids including a preservation step that includes contacting a maternal blood sample with a protective agent. The nucleic acid may be DNA or RNA or any combination thereof. The fetal nucleic acid may be cell-free DNA or RNA. The samples from which the nucleic acids may be isolated include any maternal blood sample. The fetal nucleic acids may be located in maternal plasma. The method disclosed herein allows for the efficient isolation and preservation of fetal nucleic acids while avoiding confusion with maternal nucleic acids that enter a blood sample due to maternal cell lysis after blood draw.

The process for improved fetal nucleic acid isolation from a maternal blood sample begins by contacting a blood sample with a protective agent containing an active ingredient to maintain the integrity of the components within the sample. Ingredients that may be used include, but are not limited to, diazolidinyl urea, imidazolidinyl urea, dimethoylol-5,5-dimethylhydantoin, dimethylol urea, 2-bromo-2.-nitropropane-1,3-diol, oxazolidines, sodium hydroxymethyl glycinate, 5-hydroxymethoxymethyl-1-1aza-3,7-dioxabicyclo[3.3.0]octane, 5-hydroxymethyl-1-1aza-3,7dioxabicyclo[3.3.0]octane, 5-hydroxypoly[methyleneoxy]methyl-1-1aza-3,7dioxabicyclo[3.3.0]octane, quaternary adamantine, 2-aminoacetic acid or any combination thereof. Preferred ingredients are selected from the group consisting of diazolidinyl urea (DU), imidazolidinyl urea (IDU), and any combination thereof.

The protective agent may consist essentially of the active ingredient. It may be at least about 10%, 50%, or even 80% by volume of the protective agent. For instance, the amount of active ingredient within the protective agent used may be generally about 100 to about 800 grams per liter. The amount of active ingredient within the protective agent may be at least about 25 grams per liter or even 50 grams per liter. The amount of active ingredient within the protective agent may be less than about 1500 grams per liter or even 1200 grams per liter. For example, the protective agent may comprise about 0.05 to about 0.4 grams of a formaldehyde releaser preservation agent (e.g., IDU) per 0.2 ml of the total protective agent.

As used throughout the present teachings, the protective agent composition preferably is substantially non-toxic. For example, the methods herein (and compositions used herein) may be free of separately adding and/or handling of any materially significant concentration (e.g., less than about 1% by weight, more preferably less than about 2000 parts per million, more preferably less than about 1000 parts per million, and still more preferably less than about 500 parts per million) of formaldehyde and/or paraformaldehyde prior to any contact with a blood product sample.

The protective agent may include a nuclease inhibitor in a suitable amount to prevent DNase and RNase activity from further decreasing (e.g. by at least about 10% by weight, and more preferably at least about 50% by weight) the quality and amount of fetal nucleic acids recoverable from the blood sample as compared with a sample that does not include a nuclease inhibitor. Nuclease inhibitors that may be used include, but are not limited to diethyl pyrocarbonate, ethanol, aurintricarboxylic acid (ATA), formamide, vanadyl-ribonucleoside complexes, macaloid, ethylenediamine tetraacetic acid (EDTA), proteinase K, heparin, hydroxylamine-oxygen-cupric ion, bentonite, ammonium sulfate, dithiothreitol (DTT), beta-mercaptoethanol, cysteine, dithioerythritol, tris(2-carboxyethyl) phosphene hydrochloride, or a divalent cation such as $Mg^{+2}$, $Mn^{+2}$, $Zn^{+2}$, $Fe^{+2}$, $Ca^{+2}$, $Cu^{+2}$ or any combination thereof. Further, the protective agent may be substantially free of guanidinium salts, sodium dodecyl sulfate (SDS), or any combination thereof.

The initial contacting of the blood sample may be for a time sufficient to inhibit one or both of maternal cell lysis, nuclease activity, or any combination thereof. Contacting may occur for at least about 10 seconds, more preferably at least about 1 minute, still more preferably at least about 2 minutes. Contacting can occur for longer periods of time. For example, contacting may be commenced substantially contemporaneously from the time of blood draw (e.g., within less than about 10 minutes of the blood draw) and it may last until nucleic acids are isolated, screened, and/or tested. The contacting step may also be employed to provide a sample with a longer shelf life. Thus, it is possible that a lapse of time of at least about 2 hours, more preferably at least about 6 hours, at least about 24 hours, at least about 7 days or even at least about 14 days can elapse between the time of blood draw (which may be substantially contemporaneous with the contacting step), and the time of any testing or screening of the sample, and/or isolation of the nucleic acids.

The protective agent may comprise an active agent in solution. Suitable solvents include water, saline, dimethyl-sulfoxide, alcohol and mixtures thereof. The protective agent may comprise diazolidinyl urea (DU) and/or imidazolidinyl urea (IDU) in a buffered salt solution. The protective agent may further comprise EDTA and 2-aminoacetic acid. Alternatively, the protective agent may contain only a fixative (e.g., an active ingredient) and may be free of any additional additives.

The amount of any active ingredient within the protective agent may generally be about 10% to about 90% by weight. The active ingredient or fixative may comprise about 70% to about 90% by weight of the protective agent. The protective agent may further contain an anticoagulant such as about 5% to about 20% by weight EDTA. The protective agent may contain about 10% by weight EDTA. The protective agent may include from about 1% to about 40% by weight of nuclease inhibitor.

The amount of active ingredient or fixative (e.g. the formaldehyde releaser) relative to the amount of EDTA may be about 1 to about 10 parts (more preferably about 2 to about 8 parts) by weight of fixative to about 1 part by weight EDTA. The amount of protective agent within a tube prior to blood draw may be about 0.05 to about 1.0 ml and more preferably about 0.1 to about 0.3 ml.

The combination of an active ingredient or fixative (e.g. the formaldehyde releaser) and anticoagulant within the protective agent results in improved ability to maintain the amount and quality of fetal DNA within a maternal blood sample. These results are believed unexpected and superior to results obtained by the use of only the fixative or only the anticoagulant. Therefore it is believed that a synergistic effect may occur when both a fixative and anticoagulant are combined. The compositions disclosed herein specifically envision the possibility to include the combination of a formaldehyde releaser and an anticoagulant.

The protective agent may be located within a specialized device, wherein the protective agent is already present in the device prior to addition of the blood sample, such as that disclosed in U.S. Patent Publication No. 2004/0137417, incorporated by reference herein. The device may be an evacuated collection container, usually a tube. The tube may be made of a transparent material that will also resist adherence of the cells within a given sample. The interior wall of the tube may be coated or otherwise treated to modify its surface characteristics, such as to render it more hydrophobic and/or more hydrophilic, over all or a portion of its surface. The tube may have an interior wall flame sprayed, subjected to corona discharge, plasma treated, coated or otherwise treated. The tube may be treated by contacting an interior wall with a substance so that the nucleic acids of interest will resist adhering to the tube walls. The surface of the tube may be modified to provide a dual functionality that simultaneously provides an appropriate balance of desired hydrophilicity and hydrophobicity, to allow collection of blood, dispersion of the protective agent disclosed herein, while resisting adhesion of nucleic acids to the inner wall of the blood collection tube.

It is possible that any coating may be a functionalized polymeric coating that includes a first polymer and one or more second monomeric and/or polymeric functionalities that are different from (e.g., chemically different from) the first polymer. The coating may include one or more copolymers (e.g., block copolymer, graft copolymer, or otherwise). For example, it may include a copolymer that includes a first hydrophobic polymeric portion, and a second hydrophilic polymeric portion. The coating may be a water based coating. The coating may optionally include an adhesion promoter. The coating may be applied in any suitable manner, it may be sprayed, dipped, swabbed, or otherwise applied onto some or all of the interior of the blood collection tube. The coating may also be applied in the presence of heat. Preferably any coating applied to the inner wall of a blood collection tube will form a sufficiently tenacious bond with the glass (e.g., borosilicate glass) or other material (e.g., polymeric material) of the tube so that it will not erode or otherwise get removed from the inner wall. Examples of suitable polymeric coatings may include silicon containing polymers (e.g., silanes, siloxanes, or otherwise); polyolefins such as polyethylene or polypropylene; polyethylene terephthalate; fluorinated polymers (e.g., polytetrafluoroethylene); polyvinyl chloride, polystyrene or any combination thereof. Examples of teachings that may be employed to coat an interior of a blood collection tube may be found in U.S. Pat. Nos. 6,551,267; 6,077,235; 5,257,633; and 5,213,765; all incorporated by reference.

The tube as described above may preferably include an anticoagulant agent and an active ingredient such as a fixative agent including but not limited to those active ingredients disclosed herein. The tube may also may further include a nuclease inhibitor. Preferably, the compounds included in the tube are in an amount sufficient to preserve maternal cell morphology and prevent cell degradation while also preventing deleterious DNase and RNase activity within the fetal cell-free nucleic acids. However, the amount of protective agent may also be sufficiently small so that any consequential dilution of the sample is substantially avoided, and cell-free nucleic acids in the sample are not materially diluted. A blood sample may be fixed simultaneously as it is drawn into the specialized tube. The tube may also be coated over an exterior wall with a protective coating (e.g., a containment barrier that helps control glass shard fragmentation) such as that disclosed in U.S. Pat. No. 7,419,832, incorporated by reference herein.

Additionally, the protective agent may be in a highly viscous or substantially solid state, such that (for example) it can be used effectively as a substantially solid state coating. Examples of such substantially solid state preservatives can be found in commonly owned co-pending U.S. application Ser. No. 12/646,204, filed Dec. 23, 2009 and incorporated by reference for all purposes. Liquid removal techniques can be performed on the protective agent in order to obtain a substantially solid state protective agent. Liquid removal conditions may be such that they result in removal of at least about 50% by weight, at least about 75% by weight, or at least about 85% by weight of the original amount of the dispensed liquid protective agent. Liquid removal conditions may be such that they result in removal of sufficient liquid so that the resulting composition is in the form of a film, gel or other substantially solid or highly viscous layer. For example it may result in a substantially immobile coating (preferably a coating that can be re-dissolved or otherwise dispersed upon contact with a blood product sample). It is possible that lyophilization or other techniques may be employed for realizing a substantially solid form of the protective agent (e.g., in the form of one or more pellet). Thus, liquid removal conditions may be such that they result in a material that upon contact with the sample under consideration (e.g., a maternal blood sample) the protective agent will disperse in the sample, and substantially preserve components (e.g., cell-free nucleic acids) in the sample. Liquid removal conditions may be such that they result in a remaining composition that is substantially free of crystallinity; has a viscosity that is sufficiently high that the remaining composition is substantially immobile at ambient temperature (e.g., it does not exhibit any visibly detectable (as seen by the naked eye) flow when held in a storage device at room temperature on an incline of at least about 45° for at least one hour); or both. A colorant may also be employed.

As discussed herein, contacting a maternal blood or plasma sample with the protective agent allows the sample to be stored for a period of time prior to isolating and testing the fetal nucleic acids. More preferably, a maternal blood or plasma sample may be drawn at one location (e.g., a health care facility), contacted with the protective agent, and later transported to a different remote location (e.g., a laboratory, such as one that is separately housed at a distance of at least about 1 km, 2 km, 3 km, or further away from the draw site) for the nucleic acid isolation and testing process. Fetal nucleic acids may be isolated from the maternal blood or plasma sample and tested for various fetal characteristics (including but not limited to chromosomal abnormalities) at the remote location and the resulting diagnostic information may then be reported to the site of the original blood draw. The fetal nucleic acid isolation process may be performed at one remote location and the resulting information can be analyzed to identify fetal characteristics including chromosomal abnormalities at a third location. Moreover, the results of the fetal nucleic acid isolation process may be sent back to the site of the initial blood draw and analyzed there. The resulting diagnostic information may then be sent to a third location or back to the remote location or the site of the initial blood draw.

At any time after the initial contact of the maternal blood or plasma sample with the protective agent, the sample can be treated to isolate the cell-free fetal nucleic acids located within the maternal blood. The nucleic acids may be isolated using any isolation method including those methods disclosed in commonly owned application Ser. No. 12/211,990, incorporated by reference herein. Preferably, the maternal blood cells will stay generally intact, so that maternal nucleic acids are not released into the sample from broken blood cells, making isolation of the fetal nucleic acids more difficult. The fixative acts to prevent cell lysis so that the maternal cells remain intact and substantially all maternal nucleic acids remain intra-cellular to avoid unwanted contamination of the cell-free fetal nucleic acids.

After the fetal nucleic acids have been isolated, they can be tested to identify various fetal characteristics including but not limited to sex of the fetus, preeclampsia in the mother, rhesus status of the fetus and the presence of any chromosomal abnormalities including but not limited to any chromosomal inversions, translocations, aneuploidies, other mutations, or any combination thereof. The methods herein thus further contemplate a step of nucleic acid testing. Testing of the fetal nucleic acids can be performed using any nucleic acid testing method including, but not limited to polymerase chain reaction (PCR), reverse transcription polymerase chain reaction (RT-PCR), quantitative real time polymerase chain reaction (Q-PCR), gel electrophoresis, capillary electrophoresis, mass spectrometry, fluorescence detection, ultraviolet spectrometry, DNA hybridization, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof.

One aspect of the teachings herein contemplates a method for isolating and testing cell-free fetal DNA from maternal plasma. The method may be performed on a single sample or on a multitude of samples (e.g., in a multi-well plate). The method may include contacting the maternal plasma sample with a protective agent. The protective agent may include a fixative as previously discussed so that the maternal cells remain intact throughout the blood draw and DNA isolation process. The protective agent may further include a DNase inhibitor to maintain the structural integrity of the fetal DNA. After contacting the maternal plasma sample with the protective agent, the sample may be centrifuged to separate the plasma and the supernatant is discarded. By contacting a maternal blood sample with the protective agent, the blood sample does not necessarily require immediate processing and may be stored for a prolonged period, such as up to about 14 days or longer at room temperature. Thus the inventions herein contemplate one or more steps of storing and/or otherwise waiting a relatively lengthy period from the time of blood draw and/or contacting until the time of screening, testing or other analysis.

Once, the sample is processed, an appropriate concentration of an agent for inducing precipitation (e.g., a composition of salt and/or alcohol) may be added to precipitate the fetal DNA containing material. An organic or other compound such as a phenol derivative or the like may be added to remove any remaining protein contaminants. Any protein contaminants that still remain may be removed by adding additional amounts of an organic or other compound such as a phenol derivative or the like. After centrifugation, ethanol may be added and the sample centrifuged again. Any remaining liquid may be removed from the sample so only the fetal DNA will remain. The finished product of isolated fetal DNA may then be contacted with a buffer.

One or more steps of incubation may be performed. Incubation may occur on ice or at any temperature between −30° C. and 70° C. For example, a sample may be incubated at about −20° C. A sample may also be stored at room temperature and thus substantially free of freezing upon blood draw.

Centrifugation may be performed at a suitable rate. For example, centrifugation may be done at about 500 to about 20,000 rpm. Centrifugation may occur at about 1,000 to 16,000 rpm. Centrifugation may be performed at about room temperature or cooler. For example, it may be performed at about 1-20° C., or still more specifically at about 4-9° C.

The following illustrates how a blood collection device in accordance with the present teachings can preserve fetal cell-free DNA and help minimize the cell-free DNA background in maternal plasma at ambient temperature. As will be seen, blood samples are drawn from healthy pregnant donors into (i) standard $K_3$EDTA (sold under the name BD Vacutainer® by Becton Dickinson of Franklin Lakes, N.J.) blood collection tubes and (ii) blood collection tubes containing the protective agent taught herein ("the protective agent of the present teachings"), and kept at ambient temperature. For example, the protective agent of the present teachings may include about 500 g/L IDU, about 81 g/L Tripotassium EDTA, and about 47 g/l glycine. The protective agent of the present teachings may be placed within a tube so that the tube contains about 0.20 ml of the protective agent. The tube containing the protective agent may receive about 10 ml of patient blood. The patient blood may be drawn directly into the tube containing the protective agent. It is believed that results shown will vary by about ±25% of that described across a range of about 300 to about 700 g/L IDU (with similar results expected for other formaldehyde releasers described herein) and from about 60 to about 100 g/L Tripotassium EDTA, and about 20 to about 60 g/L glycine. The protective agent may include roughly about 6 parts by weight IDU per about 1 part by weight EDTA, and roughly about 10 parts by weight IDU per about 1 part glycine. The protective agent may include about 80% by volume of IDU, 12.8% by volume Tripotassium EDTA, and 7.25 by volume glycine. An example of a commercially available tube in accordance with the present teachings is sold under the name Cell-Free DNA BCT by Streck, Inc., Omaha, Nebr.

For comparison purposes, a blood sample that is not treated with the compositions disclosed herein is centrifuged to cause plasma separation and cell-free DNA is extracted. Cell-free DNA from plasma is quantified by quantitative real-time PCR. These maternal blood samples (drawn into standard $K_3$EDTA tubes) show a steady reduction in the amount of fetal cell-free DNA during an extended time period (e.g., 36 hours, 7 days, 2 weeks etc.) at ambient temperature. Conversely, blood drawn into a device containing the protective agent of the present teachings shows no change in the amount of fetal cell-free DNA over the same time period.

Using maternal plasma stored in a device containing the protective agent of the present teachings for an extended period, fetal cell-free DNA may be amplified at least 10-fold (e.g., 80-fold) using whole genome amplification at the end of the extended period, and there is sufficient quantity of DNA available for meaningful analysis. Thus, use of the protective agent of the present teachings makes it possible to preserve fetal cell-free DNA for extended times as well as minimize any post-sampling maternal cell-free DNA background. Preserved in this way, fetal cell-free DNA can be amplified by whole genome amplification technology for producing sufficient amounts of fetal nucleic acids as a starting material for nucleic acid-based prenatal diagnostic tests.

For the discussion that follows, there is envisioned a protocol that employs some or all of the following steps, following direct draw of a blood sample into an evacuated blood collection tube. In accordance with the present invention, the blood sample may be contacted by a protective agent such as those protective agents described herein. The processing of nucleic acids for analysis may include a step of purifying the nucleic acids and amplifying the nucleic acids.

Samples of the treated blood (e.g., one and one half ml aliquots of blood) may be removed from each tube periodically; cell-free plasma DNA may be purified; primers and probes for the real-time PCR quantification of one or more antibody or protein sequences (e.g., β-actin, SRY, RASSF1A and/or other markers for fetal DNA) may be prepared; real-time PCR quantification of one or more antibody or protein sequences (e.g., β-actin, SRY, RASSF1A and/or other markers for fetal DNA) may be carried out; re-suspended plasma DNA may be treated with a restriction enzyme; a promoter region sequence (such as those associated with the fetal DNA markers discussed herein) may be used as a universal marker for fetal DNA; a suitable amplifier may be used to amplify fetal cell-free plasma DNA obtained from maternal blood stored in the device of the present teachings; or statistical analysis may be carried out.

Primers and probes for the real-time PCR quantification of certain antibody or protein sequences discussed herein (e.g., β-actin, RASSF1A and/or other markers for fetal DNA) may be prepared in accordance with art-disclosed teachings, such as described by Chan et al. *Clinical Chemistry* 52:2211-2218 (2006) (incorporated by reference). Primers for the Y-chromosomal sex determining region (SRY) may be prepared in accordance with art-disclosed teachings, such as Lee et al., *Blood* 93:3127-3139 (incorporated by reference). An example probe that may be used for the quantification of SRY sequence is 6FAM-ATG GCT CTA GAG AAT CCC AGA ATG CGA AAC TCA GAG A-TAMRA. Commercially available primers, probes and PCR master mix, (e.g., TaqMan® Universal PCR master mix) may be purchased from Applied Biosystems, Foster City, Calif. Plasmid DNA constructs may be prepared so that each contains a single copy of the antibody or protein sequences discussed herein (β-actin, RASSF1A, SRY, and/or other fetal DNA markers). These plasmid constructs may be used to plot the standard curves.

After re-suspension of the plasma DNA, the plasma may be treated with a restriction enzyme (e.g., 25 U of BstUI restriction enzyme, available from New England Biolabs, Ipswich, Mass.) in accordance with art-disclosed teachings, such as described by Chan et al. (2006).

Following re-suspension, a suitable amplifier (e.g., a QIAGEN REPLI-g® UltraFast Mini whole genome amplification kit available from QIAGEN, Inc., Valencia, Calif.) may be used for the step of amplifying the fetal cell-free plasma DNA obtained from maternal blood stored in the device of the present teachings. Purified cell-free DNA is prepared from a volume of plasma (e.g., at least about 100 μl, or less than about 800 μl) as described above, but is re-suspended in a small volume (e.g., at least about 0.05 μl, or less than about 10 μl) and amplified using the kit according to the manufacturer's instructions. After amplification, the sample may be diluted (e.g., by about 25-fold) prior to PCR analysis.

In verifying the protective capabilities of the compositions disclosed herein, Standard $K_3$EDTA brood collection tubes are thus compared against tubes containing the protective agent of the present teachings, which thus contains a composition that stabilizes nucleated blood cells and inhibits plasma nucleases. In the examples and results discussed below, statistical analysis is carried out using software available at the Tools for Science website of the Physics Department, College of Saint Benedict Saint John's University, St. Joseph, Minn. Paired Student's t test is used and $P<0.05$ is considered statistically significant.

Example 1

Figure 2:
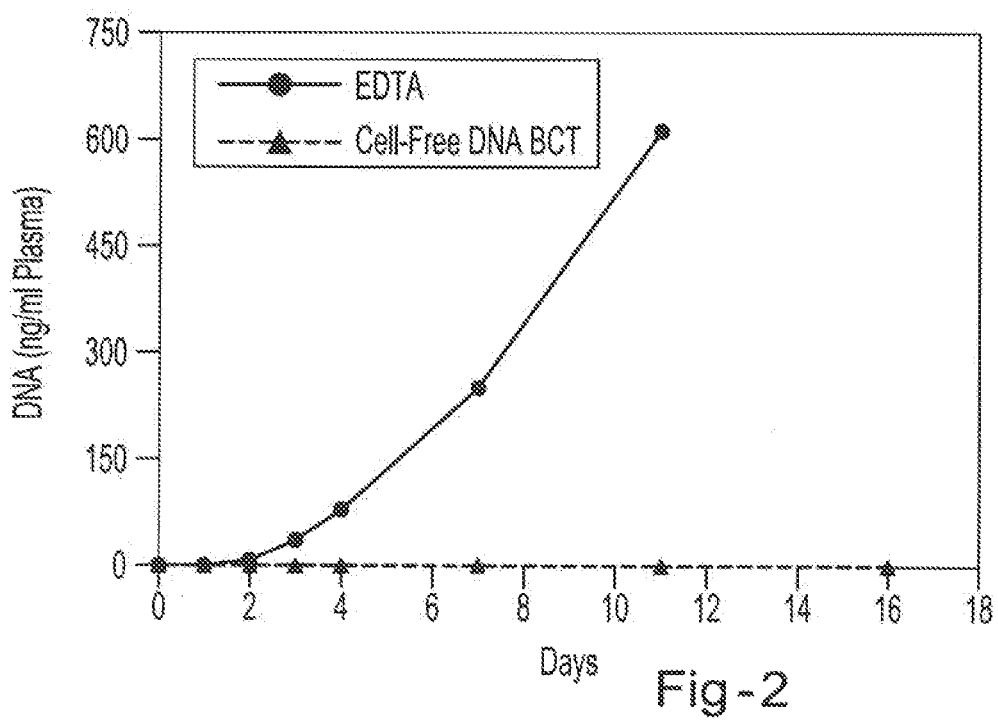
FIG. 2 is an illustrative graphic representation showing the relative amounts of Y-chromosomal DNA present as a result of male white blood cell leakage within two female blood samples over time; again there is seen a plot of "cell-free DNA BCT" that extends substantially entirely along the x-axis at a y-axis value of zero (0) DNA.

Blood samples are taken from a female donor and a male donor. The female blood sample is transferred into two tubes, tube A containing about 500 g/L IDU, about 80 g/L Tripotassium EDTA, and about 50 g/L glycine and tube B containing only the Tripotassium EDTA. Both tubes are stored at room temperature. White blood cells from the male blood sample are isolated and spiked into both tube A and tube B. 3 ml of blood are taken from each tube on day 0, day 1, day 2, day 3, day 4, day 7 and day 11. Each sample is centrifuged at room temperature at 800 g for 10 minutes and the upper plasma layer is transferred to a new tube and further centrifuged at 1500 g at room temperature for 10 minutes. The free circulating DNA in each tube is then purified using the NucleoSpin® Plasma XS kit available from Macherey-Nagel Inc., Bethlehem, Pa. The samples are then amplified by Real Time PCR amplification of a fragment of the Y-chromosome (using iQ SYBR Green Supermix reagents available from BIO-RAD Laboratories (Hercules, Calif.)). Any rupture of the male white blood cells during sample processing will cause Y-chromosomal DNA to be detectable within the female blood sample. Tube A shows no Y-chromosomal DNA presence within the plasma sample, while the amount of Y-chromosomal DNA identified in tube B increases at each measurement, indicating male white blood cell rupture in tube B. The expected results of this example are shown in graphic format at FIG. 2, and supports that use of the compositions disclosed herein are capable of substantially preventing lysis of the blood cells spiked into the samples.

Example 2

Figure 3:
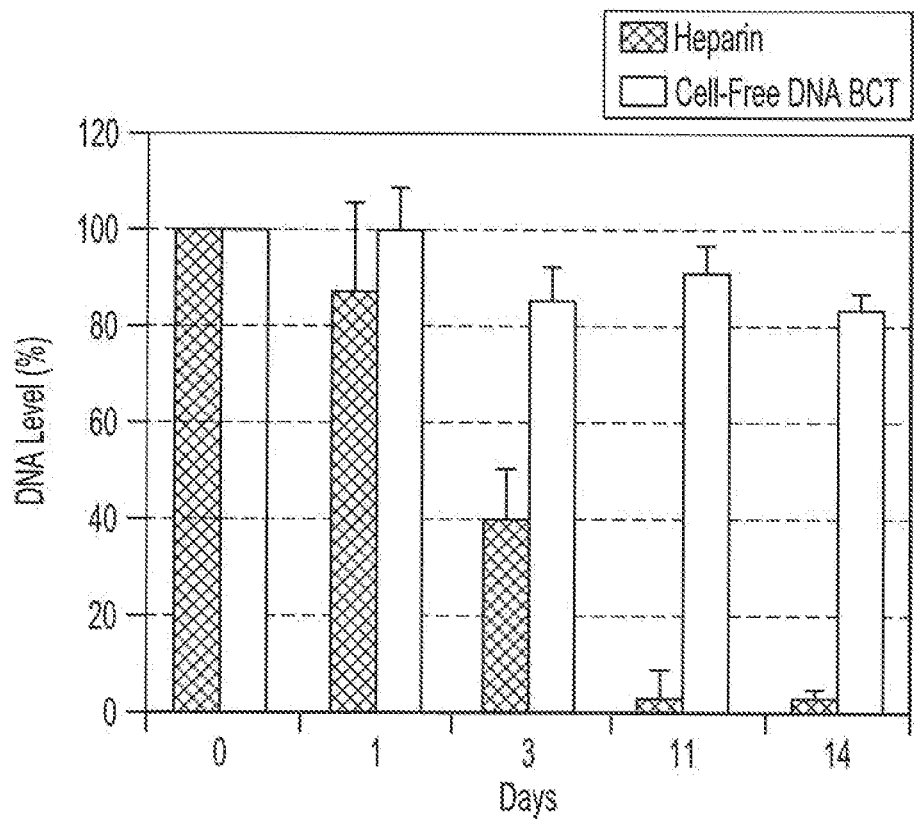
FIG. 3 is an illustrative graphic representation showing the relative amounts of cell-free DNA present within blood samples over time using lambda DNA as a marker.

Blood samples from the same donor are drawn into two different types of blood collection tubes. One tube contains 500 g/L IDU, 81 g/L Tripotassium EDTA and 47 g/L glycine. The other tube contains only Heparin. All samples are centrifuged at 2100 g for 30 minutes at room temperature to separate the plasma. The plasma is then transferred to new tubes and non-human (lambda) DNA is then spiked into the plasma tubes. The spiked samples are then stored at room temperature for 0, 1, 2, 3, 4, 7, 11, and 14 days. Free circulating DNA is purified using the QIAamp® DNA Blood Mini Kit available from QIAGEN Inc. (Valencia, Calif.). DNA is extracted from each plasma sample. The samples are then amplified by Quantitative PCR (using iQ SYBR Green Supermix reagents available from BIO-RAD Laboratories (Hercules, Calif.)) to identify the amount of lambda DNA present. Results show a consistent relative percentage of lambda DNA presence at each measurement, indicating little if any decline in the percentage of cell-free DNA in the plasma samples contacted by both IDU and Tripotassium EDTA. The amount of lambda DNA decreases at every consecutive measurement in those samples contacted with only Heparin, indicating a gradual decline in the relative percentage of cell-free DNA. The expected results of this example are shown in graphic format at FIG. 3. This example confirms that the compositions of the present invention are able to maintain the integrity and amount of DNA present in a blood sample.

Example 3

Figure 4:
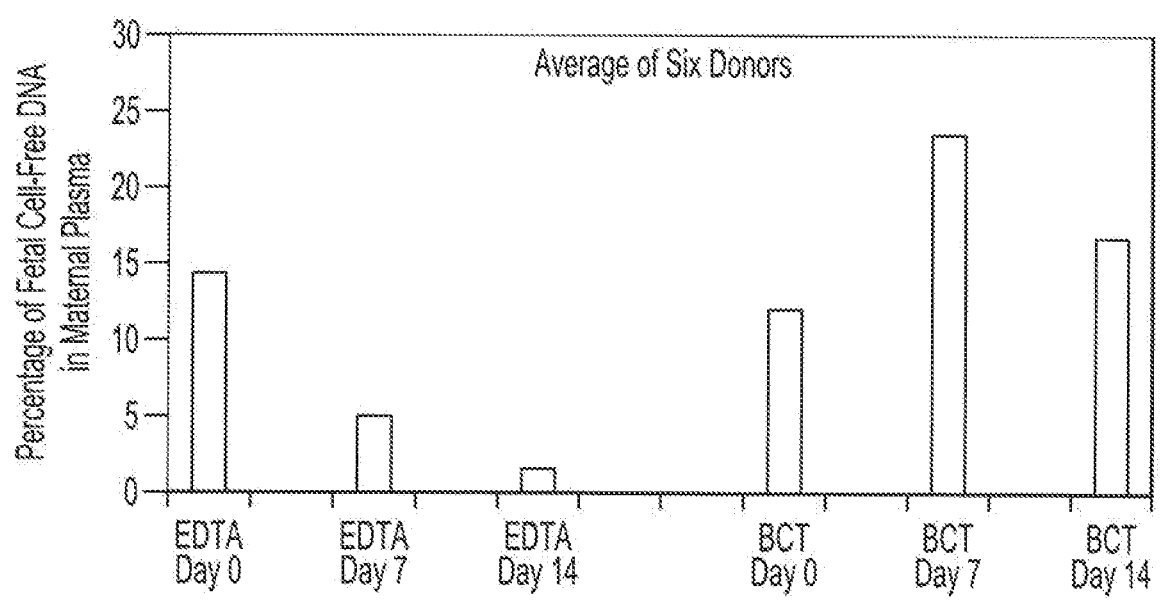
FIG. 4 is an illustrative graphic representation showing the relative amounts of cell-free fetal DNA present within two blood samples over time using the RASSF1A promoter region as a marker.

Two maternal blood samples from the same donor are drawn into two separate blood collection tubes. One tube contains about 500 g/L IDU, about 80 g/L Tripotassium EDTA, and about 50 g/L glycine. The other tube contains only the Tripotassium EDTA. Both tubes are stored at room temperature and 1 ml aliquots of blood are removed from each tube on day 0, day 7, and day 14 and plasma is separated. All samples are centrifuged at 800 g for 10 minutes at room temperature to separate the plasma. The plasma is then transferred into new tubes and centrifuged at 1500 g for 10 minutes at room temperature. Free circulating DNA is purified using the NucleoSpin® Plasma XS kit available from Macherey-Nagel Inc., Bethlehem, Pa. DNA is extracted from each plasma sample and eluted in 60 µl of elution buffer. An amount of 32 µl of eluted DNA is digested with 40 U of BstU 1 enzyme at 60° for 6 hours. The samples are then amplified by Real Time PCR (using TaqMan® RT PCR reagents available from Applied Biosystems, Foster City, Calif.) using primers for RASSF1A promoter region. Results show a consistent relative percentage of RASSF1A presence at each measurement, indicating little if any decline in the percentage of fetal cell-free DNA in the maternal plasma samples contacted by both IDU and Tripotassium EDTA. The amount of RASSF1A decreases at every consecutive measurement in those samples contacted with only the Tripotassium EDTA, indicating a gradual decline in the relative percentage of fetal cell-free DNA. The results of this example are shown in graphic format at FIG. 4.

Figure 5:
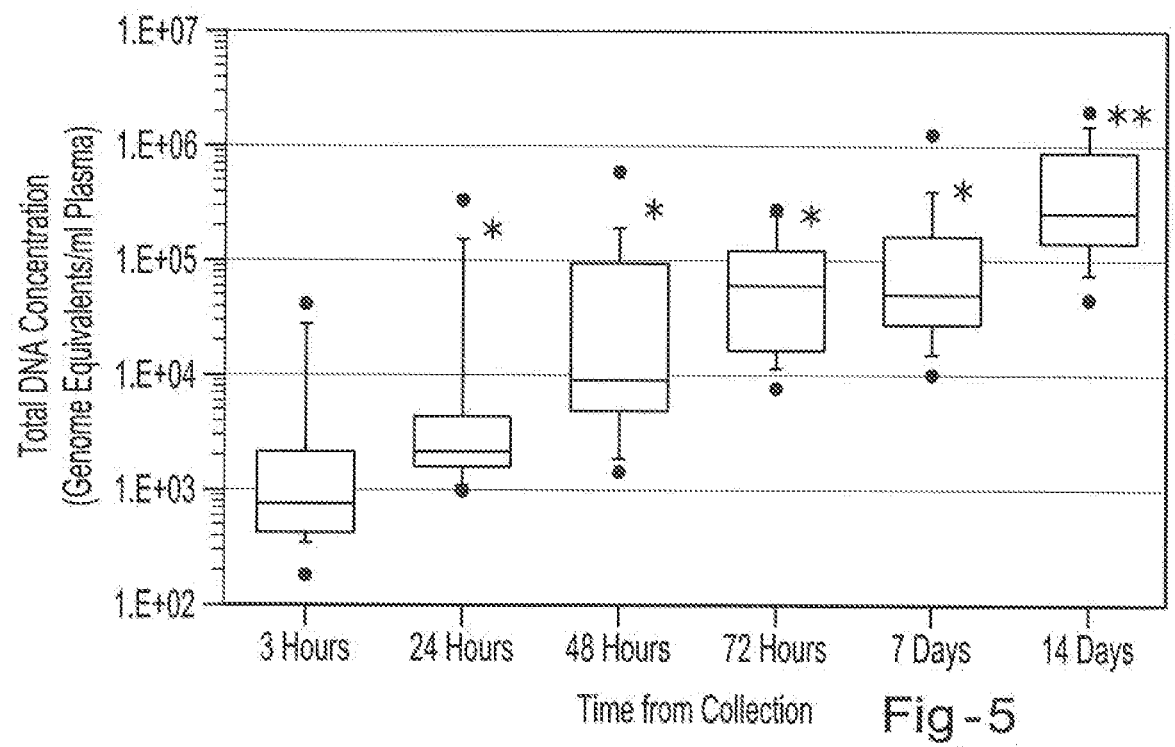
FIG. 5 is an illustrative graphic representation showing the relative amounts of plasma DNA over time in a blood sample drawn into standard $K_3EDTA$ tubes. In each box-plot, the total amount of cell-free plasma DNA is represented as genome equivalents per milliliter of plasma (GE/ml). The line inside of the box indicates the median value. The limits of the box represent the $75^{th}$ and $25^{th}$ percentiles. The upper and lower error bars indicate the 10th and 90th percentiles, respectively. The uppermost and lowermost dots indicate the maximum and minimum values. The y-axis is in logarithmic scale.

FIG. 5 shows the expected result of ex-vivo incubation of maternal blood when drawn into standard $K_3$EDTA tubes on the cell-free DNA concentration in plasma. Initially (3 hrs), the median cell-free DNA concentration is found to be 762 genome equivalents per ml of plasma (GE/ml) which increased markedly over time. Compared to the initial 3 hrs value, statistically significant increases are observed in the cell-free DNA concentration at 24 hrs ($P<0.05$), 48 hrs ($P<0.05$), 72 hrs ($P<0.05$), 7 days ($P<0.05$) and 14 days ($P$ 0.001). This steady increase may reflect the lysis of nucleated blood cells and the subsequent release of cellular genomic DNA into the plasma that continued for 14 days.

Figure 6:
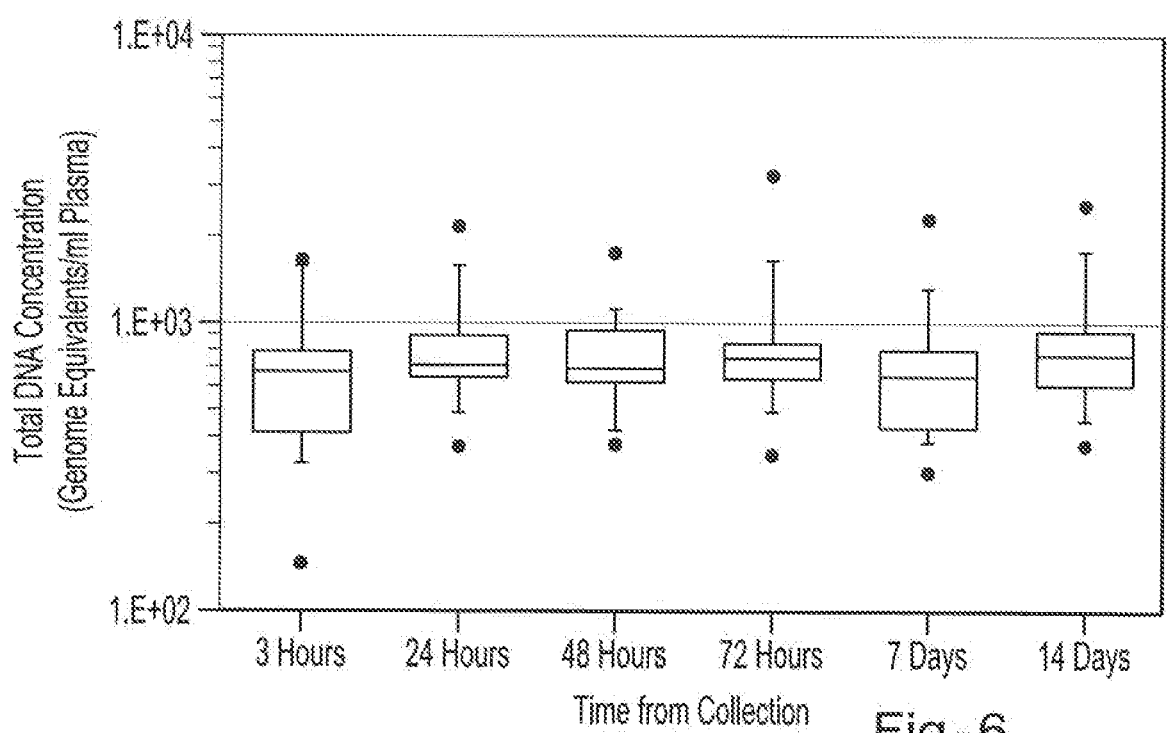
FIG. 6 is an illustrative graphic representation showing the relative amounts of plasma DNA over time in a blood sample drawn into a device of the present teachings. In each box-plot, the total amount of cell-free plasma DNA is represented as genome equivalents per milliliter of plasma (GE/ml). The line inside of the box indicates the median value. The limits of the box represent the $75^{th}$ and $25^{th}$ percentiles. The upper and lower error bars indicate the 10th and 90th percentiles, respectively. The uppermost and lowermost dots indicate the maximum and minimum values. The y-axis is in logarithmic scale.

FIG. 6 illustrates the expected effect of ex-vivo incubation of maternal blood drawn into tubes containing the protective agent of the present teachings on the plasma cell-free DNA concentration. Here, an initial median cell-free DNA concentration of 672 GE/ml does not increase significantly throughout the entire 14 day experimental period, indicating that an enhanced integrity of nucleated blood cells is observed. After 3 hrs of incubation, a comparison of the plasma cell-free DNA concentration in $K_3$EDTA tubes and tubes containing the protective agent of the present teachings showed a statistically significant difference ($P<0.05$). The mean cell-free DNA concentration in $K_3$EDTA tubes is 6341 GE/ml whereas it is 680 GE/ml in those tubes containing the protective agent of the present teachings. The higher cell-free plasma DNA concentration in the $K_3$EDTA tube compared to those tubes containing the protective agent of the present teachings indicates that cellular DNA is released into plasma by nucleated blood cell lysis.

Figure 7:
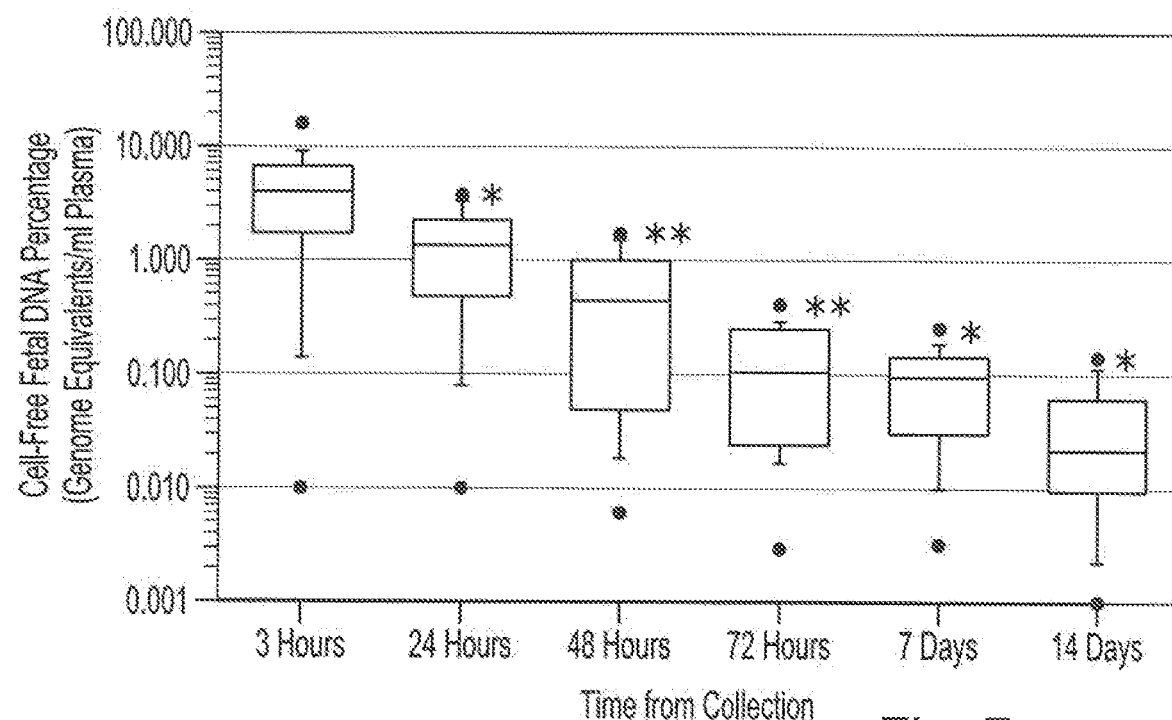
FIG. 7 is an illustrative graphic representation showing the relative amounts of fetal cell-free DNA over time in a blood sample drawn into standard $K_3EDTA$ tubes. In each box plot, the percentage of cell-free plasma DNA is represented as genome equivalents per milliliter of plasma (GE/ml). The line inside of the box indicates the median value. The limits of the box represent the $75^{th}$ and $25^{th}$ percentiles. The upper and lower error bars indicate the $10^{th}$ and $90^{th}$ percentiles, respectively. The upper most and lower most dots indicate the maximum and minimum values. The y-axis is in logarithmic scale. Over time, a statistically significant decrease in the percentage of fetal cell-free DNA is seen only in $K_3EDTA$ tubes (*$P<0.05$, **$P≤0.01$ by paired Student's t test).

FIG. 7 shows the expected effect of ex vivo incubation on the fetal cell-free DNA in maternal plasma in $K_3$EDTA blood collection tubes. A statistically significant decrease in the percentage of fetal cell-free DNA is observed. This downward trend in the median values of the percentage of fetal cell-free DNA; 4.05, 1.33, 0.45, 0.11, 0.10 and 0.023 (at 3 hrs, 24 hrs, 48 hrs, 72 hrs, 7 days and 14 days, respectively), demonstrates that $K_3$EDTA tubes are not capable of maintaining the fetal cell-free DNA percentage in maternal plasma at a constant level.

Figure 8:
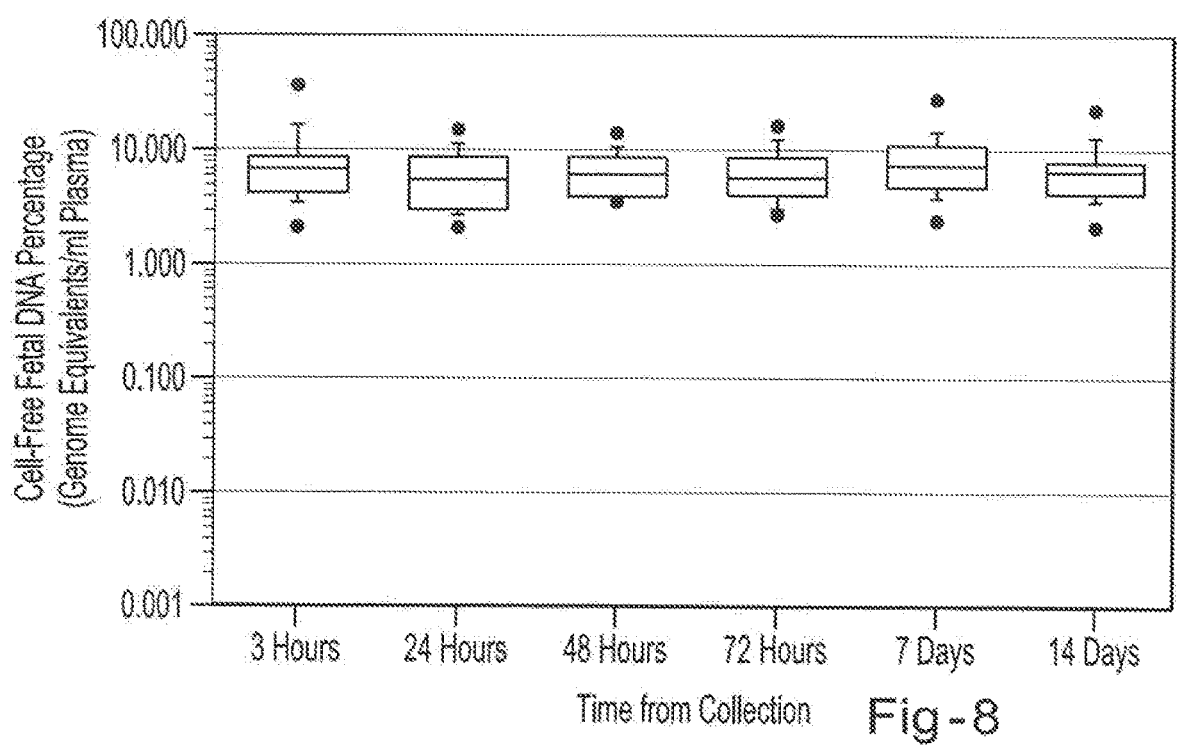
FIG. 8 is an illustrative graphic representation showing the relative amounts of fetal cell-free DNA over time in a blood sample drawn into a device of the present teachings. In each box plot, the percentage of cell-free plasma DNA is represented as genome equivalents per milliliter of plasma (GE/ml). The line inside of the box indicates the median value. The limits of the box represent the $75^{th}$ and $25^{th}$ percentiles. The upper and lower error bars indicate the $10^{th}$ and $90^{th}$ percentiles, respectively. The upper most and lower most dots indicate the maximum and minimum values. The y-axis is in logarithmic scale. Over time, a statistically significant decrease in the percentage of fetal cell-free DNA is seen only in $K_3EDTA$ tubes (*$P<0.05$, **$P≤0.01$ by paired Student's t test).

FIG. 8 shows the expected effect of ex-vivo incubation on the fetal cell-free DNA in maternal plasma when contacted by the protective agent of the present teachings. Here, the percentage of fetal cell-free DNA does not change significantly in the trend of median values; 6.8, 5.5, 6.2, 6.1, 6.8 and 6.5 at 3 hrs, 24 hrs, 48 hrs, 72 hrs, 7 days and 14 days, respectively.

Figure 9:
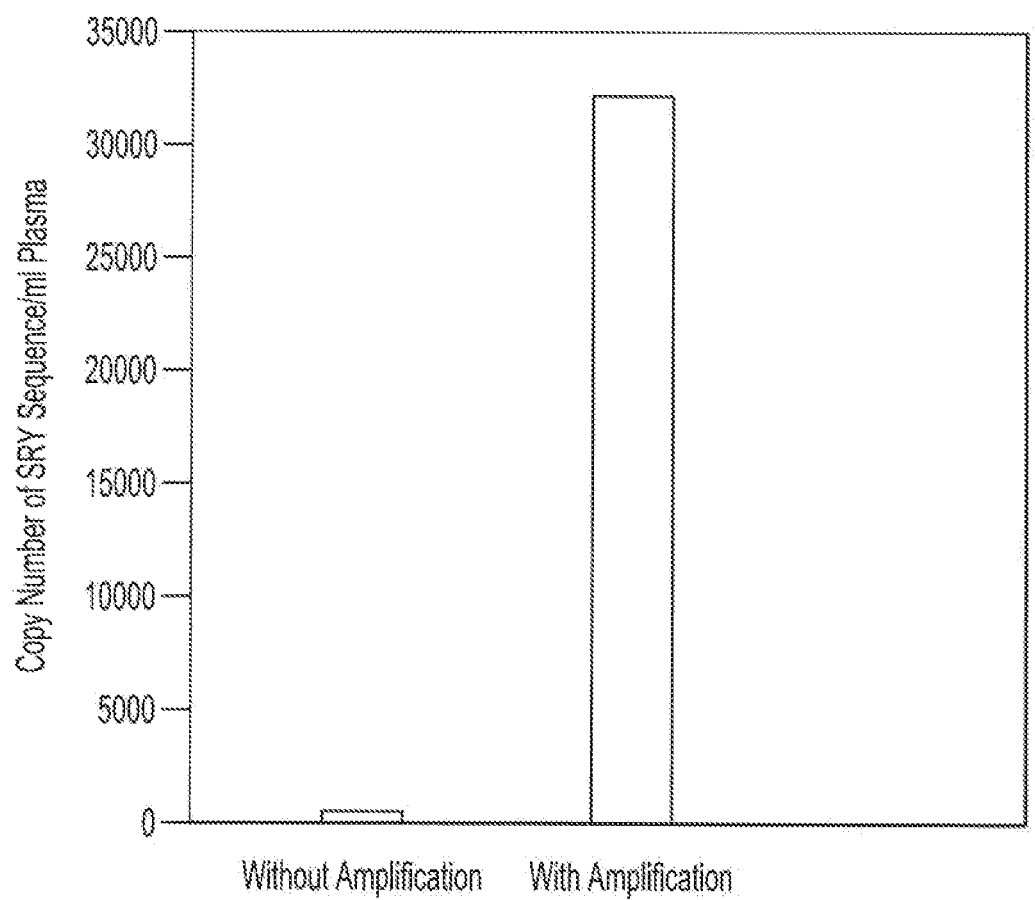
FIG. 9 is an illustrative graphic representation showing amplification of fetal cell-free DNA from maternal plasma by whole genome amplification (WGA). One aliquot (without amplification) is used directly to quantify (by real-time PCR) the Y chromosomal SRY sequence from maternal plasma (an indicator of fetal DNA in maternal plasma). The other aliquot (with amplification) is subjected to WGA and then SRY sequence quantification by real-time PCR is performed. Enrichment in fetal cell-free DNA from maternal plasma by eighty fold is observed with WGA. A plasmid DNA construct containing a single copy of the Y chromosomal SRY sequence is used to plot the standard curve for the quantification.

In further testing, donor plasma that had tested positive for the Y chromosome (data not shown) was used for whole genome amplification (WGA). By real-time PCR, 398 SRY DNA copies are detected without WGA, whereas 32,300 SRY DNA copies are detected following WGA. This represents enrichment in fetal cell-free DNA by at least about 10 fold, 20 fold, 40 fold or even 80 fold from maternal plasma that had been stored in a device containing the protective agent of the present teachings at ambient temperature for the same period (e.g., 2 weeks) (FIG. 9).

As discussed in reference to FIG. 5, maternal blood collected into standard $K_3$EDTA tubes shows a 7-fold and 98-fold increase in total cell-free DNA in maternal plasma at 24 hrs and 14 days as compared to 3 hrs, respectively. However, total cell-free DNA concentration is constant at ambient temperature for up to 14 days in maternal blood contacted by the protective agent of the present teachings (FIG. 6). Without intending to be bound by theory, this indicates that the chemicals present in the protective agent of the present teachings are able to fix the nucleated blood cells thereby preventing apoptosis, cell death and cell lysis associated cellular genomic DNA release into plasma. A comparison of total cell-free DNA concentrations in $K_3$EDTA and the device of the present teachings at initial time point (3 hrs) show a statistically significant difference. The mean total cell-free DNA concentration in $K_3$EDTA tube at 3 hrs is 6341 GE/ml, whereas in a tube containing the protective agent of the present teachings, it is only 680 GE/ml. This multi-fold (e.g., 9-fold) increase in total cell-free DNA concentration in the samples contacted by only $K_3$EDTA as compared to samples contacted by the protective agent of the present teachings may result from increased cellular genomic DNA release from nucleated blood cell apoptosis, death and lysis during post blood draw ex vivo incubation and sample processing, and may be substantially avoided by use of the teachings herein.

FIG. 7 shows the expected effect of ex vivo incubation (of blood drawn into $K_3$EDTA tube) on fetal cell-free DNA percentage in maternal blood plasma. There is a statistically significant decrease in fetal cell-free DNA percentage over time. The major contributor to this steady decrease in fetal cell-free DNA percentage may be the increased background maternal cell-free DNA, as fetal cell-free DNA degradation may occur due to nuclease action. In contrast, as shown in FIG. 8, fetal cell-free DNA percentage of maternal blood contacted by the protective agent of the present teachings may be substantially constant over time at ambient temperature. It is believed that this protective effect may be the result of the chemicals present in the protective agent of the present teachings that stabilize blood cells preventing cellular DNA release as well as nuclease inhibitory activity that protect fetal cell-free DNA from degradation. Thus, the teachings herein contemplate treating a sample in a matter such that limits the deleterious effects of DNase and RNase on the fetal nucleic acids present in the plasma.

As evidenced by the examples and testing results disclosed herein, fetal cell-free DNA found in maternal blood plasma is a valuable source for noninvasive prenatal diagnosis. However, a major factor that limits the effective use of fetal cell-free DNA in nucleic acid-based prenatal testing is that the total DNA concentration present in maternal plasma, comes largely from the mother herself. Thus, samples may be free of cell-free DNA attributable to apoptosis, cell death and lysis of nucleated maternal blood cells. This may be the case after about 4 hours from blood draw, 6 hours from blood draw, or even 24 hours from blood draw.

When the integrity of a DNA target is compromised, the targeted DNA sequence fails to be amplified. Since most of the DNA-based prenatal diagnostic tests depend on subsequent DNA amplification, it is important to protect the integrity of rare DNA targets such as fetal cell-free DNA during all pre-analytical procedures. Here, fetal cell-free DNA percentage is determined by real-time quantitative PCR. FIG. 8 shows that fetal cell-free DNA percentage stays substantially constant for up to 14 days and provides evidence that the protective agent of the present teachings can protect the integrity of fetal cell-free DNA at ambient temperature for up to 14 days.

One of the factors that limit the use of fetal cell-free DNA in maternal plasma in noninvasive prenatal diagnosis is its low relative level in maternal plasma. Therefore, we amplify fetal cell-free DNA in maternal plasma by whole genome amplification (WGA). A first trimester pregnant donor with a male fetus is identified by amplifying Y chromosomal SRY region sequence. Amplification of cell-free plasma DNA obtained from this donor by WGA and subsequent detection of Y chromosomal SRY region sequence by real-time PCR shows a multi-fold (e.g., at least 10, 20, 40 or ~80-fold) increase in fetal cell-free DNA concentration (FIG. 9). When cell-free DNA for WGA isolated from blood contacted by the protective agent of the present teachings and stored at ambient temperature for 14 days, results are expected to provide strong evidence that the protective agent of the present teachings is able to preserve the integrity of long fetal cell-free DNA molecules that are required for WGA.

This new methodology can be used to circumvent many existing pre-analytical issues that can affect the detection of fetal cell-free DNA in maternal blood. Since the protective agent of the present teachings stabilizes nucleated blood cells and inhibits plasma nucleases, it is possible to store maternal blood samples in a device containing the protective agent of the present teachings at ambient temperature for up to 14 days without any increase in background maternal cell-free DNA concentration and without any alteration in cell-free DNA integrity. Methods herein contemplate such storing. The methods herein also contemplate using the device of the present teachings to draw maternal blood for noninvasive prenatal diagnosis when blood drawing and nucleic acid testing are not done at the same location. The methods herein thus may be free of any step of immediate separation of plasma after blood draw, freezing of the plasma (e.g., at −80° C.) or both, for shipping. The methods herein may also be free of any use of magnetic beads or particles of any kind. The methods herein may be free of any addition of formaldehyde to the blood sample immediately following the blood draw.

The examples and testing results discussed above demonstrate an unexpected synergistic effect occurring only in blood samples contacted by both a fixative and an anticoagulant, or more specifically, by IDU, EDTA and glycine. Maternal blood samples contacted by only a fixative or only an anticoagulant do not demonstrate the ability to maintain the integrity of the maternal blood cells or the integrity of the fetal nucleic acids. The combined effect of the IDU, EDTA and glycine far exceeds any expectations based on the effect, or lack thereof, of the IDU or EDTA or glycine used alone.

It will be appreciated that concentrates or dilutions of the amounts recited herein may be employed. In general, the relative proportions of the ingredients recited will remain the same. Thus, by way of example, if the teachings call for 30 parts by weight of a Component A, and 10 parts by weight of a Component B, the skilled artisan will recognize that such teachings also constitute a teaching of the use of Component A and Component B in a relative ratio of 3:1. Teachings of concentrations in the examples may be varied within about 25% (or higher) of the stated values and similar results are expected. Moreover, such compositions of the examples may be employed successfully in the present methods to isolate fetal nucleic acids (e.g., cell-free fetal DNA).

It will be appreciated that the above is by way of illustration only. Other ingredients may be employed in any of the compositions disclosed herein, as desired, to achieve the desired resulting characteristics. Examples of other ingredients that may be employed include antibiotics, anesthetics, antihistamines, preservatives, surfactants, antioxidants, unconjugated bile acids, mold inhibitors, nucleic acids, pH adjusters, osmolarity adjusters, or any combination thereof.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The invention claimed is:

1. A method for stabilizing, storing, isolating and analyzing cell-free fetal nucleic acid comprising:
   drawing a blood sample including a plasma containing donor cellular nucleic acid and cell-free nucleic acid including cell-free fetal nucleic acid directly into an evacuated blood collection tube containing about 0.05 ml to 1.0 ml of a protective agent wherein the protective agent is a solution formed from ingredients including:
   a) 0.1 to 3 g/ml of imidazolidinyl urea;
   b) glycine; and
   c) EDTA;
   wherein an amount of imidazolidinyl urea relative to an amount of glycine is 10 parts by weight of imidazolidinyl urea to 1 part by weight glycine; storing the blood sample including the plasma for 1 to 14 days,
   separating the plasma from the blood sample;
   isolating the cell-free nucleic acid from the plasma of the stabilized blood sample;

and analyzing at least the cell-free fetal nucleic acid isolated from the plasma of the stabilized blood sample;
wherein the blood sample and the plasma is not frozen prior to the step of isolating.

2. The method of claim 1, wherein the analyzing step includes contacting the cell-free fetal nucleic acid with an enzyme, an amplifier or both.

3. The method of claim 1, wherein the evacuated blood collection tube into which the blood sample is drawn includes a polymeric coating on an interior of the tube.

4. The method of claim 1, wherein a concentration of the imidazolidinyl urea within the protective agent prior to the drawing step is between 0.4 g/ml and 0.8 g/ml.

5. The method of claim 2, wherein an amount of imidazolidinyl urea within the protective agent and upon contact with the blood sample is less than about 20 mg/ml of the total combined blood sample and protective agent.

6. The method of claim 1, wherein the step of storing is at room temperature.

7. The method of claim 1, wherein the protective agent prior to the drawing step contains less than 1000 parts per million formaldehyde.

8. The method of claim 6, wherein the protective agent prior to the drawing step contains less than 1000 parts per million formaldehyde.

9. A method for stabilizing, storing and isolating cell-free fetal nucleic acid comprising:
contacting a drawn blood sample containing donor cellular nucleic acid and cell-free nucleic acid including the cell-free fetal nucleic acid with a protective agent that is a solution formed from ingredients including:
(i) about 300 g/l to about 700 g/l imidazolidinyl urea;
(ii) about 20 g/l to about 60 g/l glycine; and
(iii) about 60 g/l to about 100 g/l of EDTA;
wherein the solution includes a solvent;
allowing a period of time to lapse; and
after the period of time has elapsed, separating a plasma from the drawn blood sample and isolating the cell-free nucleic acid from the plasma, wherein the cell-free nucleic acid is free of cell-free nucleic acid attributable to apoptosis, cell death and lysis of nucleated maternal blood cells post blood draw.

10. The method of claim 9, wherein the period of time is at least 24 hours without freezing of the contacted drawn blood sample.

11. The method of claim 4, wherein the evacuated blood collection tube containing the protective agent receives about 10 ml blood.

12. The method of claim 1, wherein the step of storing is for 7 to 14 days.

13. The method of claim 9, wherein the period of time is 7 to 14 days, without freezing of the contacted drawn blood sample.

14. A method for stabilizing, storing, isolating and analyzing cell-free fetal nucleic acid comprising:
drawing about a 10 ml blood sample containing donor cellular nucleic acid and a plasma comprising cell-free nucleic acid, including a cell-free fetal nucleic acid, directly into an evacuated blood collection tube containing about 0.1 ml to about 0.3 ml protective agent that is formed from a solvent, and ingredients consisting of:
(i) about 300 g/l to about 700 g/l imidazolidinyl urea;
(ii) about 20 g/l to about 60 g/l glycine; and
(iii) about 60 g/l to about 100 g/l EDTA;
wherein the protective agent contacts and stabilizes storing the blood sample including the plasma for 1 to 14 days;
separating the plasma from the stored blood sample;
isolating the cell-free nucleic acid, including the cell-free fetal nucleic acid, from the plasma; and
amplifying the isolated fetal cell-free nucleic acid by at least 80-fold using whole genome amplification (WGA);
wherein the blood sample and the plasma is not frozen prior to the step of isolating.

15. A cell-free fetal nucleic acid based screening procedure utilizing the method of claim 1.

16. The method of claim 1, wherein the ingredients consist of the glycine, the imidazolidinyl urea, and the EDTA; and the protective agent is formed of only the solvent and the ingredients.

17. The method of claim 16, wherein during storage, the collection tube contains only the drawn blood sample and the protective agent.

18. The method of claim 14, wherein the protective agent is formed of only the solvent and the ingredients.

19. The method of claim 18, wherein during storage, the collection tube contains only the drawn blood sample and the protective agent.

20. The method of claim 9, wherein from 3.4% to 6.2% of the cell-free nucleic acid in the plasma is the cell-free fetal nucleic acid.

\* \* \* \* \*